US008895281B2

(12) United States Patent
Song et al.

(10) Patent No.: US 8,895,281 B2
(45) Date of Patent: Nov. 25, 2014

(54) METHOD FOR PREPARING A SITE-SPECIFIC PHYSIOLOGICALLY ACTIVE POLYPEPTIDE CONJUGATE

(75) Inventors: Dae Hae Song, Hwaseong-si (KR); Jae Hee Shin, Suwon-si (KR); Jae Min Lee, Seoul (KR); Young Kyung Park, Suwon-si (KR); Se Chang Kwon, Seoul (KR); Gwan Sun Lee, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 13/255,199

(22) PCT Filed: Mar. 18, 2010

(86) PCT No.: PCT/KR2010/016740

§ 371 (c)(1), (2), (4) Date: Sep. 7, 2011

(87) PCT Pub. No.: WO2010/107256

PCT Pub. Date: Sep. 23, 2010

(65) Prior Publication Data

US 2012/0003712 A1 Jan. 5, 2012

(30) Foreign Application Priority Data

Mar. 20, 2009 (KR) ........................ 10-2009-0023953

(51) Int. Cl.

| | |
|---|---|
| ***C12N 9/00*** | (2006.01) |
| ***C07K 7/04*** | (2006.01) |
| ***C07K 14/00*** | (2006.01) |
| ***C07K 1/107*** | (2006.01) |
| ***A61K 47/48*** | (2006.01) |
| ***C07K 14/575*** | (2006.01) |
| ***C07K 14/605*** | (2006.01) |
| ***C07K 14/62*** | (2006.01) |

(52) U.S. Cl.

CPC ......... *C07K 1/1077* (2013.01); *A61K 47/48215* (2013.01); *C07K 14/575* (2013.01); *C07K 14/605* (2013.01); *C07K 14/62* (2013.01)

USPC ............ 435/183; 530/300; 530/350; 530/402

(58) Field of Classification Search

USPC .......................... 435/183; 530/300, 350, 402

See application file for complete search history.

(56) References Cited

U.S. PATENT DOCUMENTS

| | | | | |
|---|---|---|---|---|
| 5,981,709 | A | 11/1999 | Greenwald et al. | |
| 2004/0180054 | A1 | 9/2004 | Kim et al. | |
| 2005/0176108 | A1 | 8/2005 | Kim et al. | |
| 2006/0276586 | A1 | 12/2006 | Kim et al. | |
| 2007/0083006 | A1* | 4/2007 | Hinds et al. | 525/54.1 |

FOREIGN PATENT DOCUMENTS

| | | | |
|---|---|---|---|
| EP | 0 922 446 | A1 | 6/1999 |
| JP | 2007-526234 | A | 9/2007 |
| JP | 2008-143897 | A | 6/2008 |
| KR | 10-2004-0081378 | A | 9/2004 |
| KR | 10-2004-0086930 | A | 10/2004 |
| WO | 96/41813 | A2 | 12/1996 |
| WO | 00/66629 | A1 | 11/2000 |
| WO | 2004/093823 | A2 | 11/2004 |
| WO | 2006/076471 | A2 | 7/2006 |
| WO | 2008/051383 | A2 | 5/2008 |
| WO | 2009/011544 | A2 | 1/2009 |

OTHER PUBLICATIONS

Taiwanese Patent Office, Taiwanese Office Action issued in corresponding TW Application No. 099108144, dated Aug. 22, 2012.
Russian Patent Office, Russian Office Action issued in corresponding RU Application No. 2011142332, dated Jun. 22, 2012.
European Patent Office, European Search Report issued in corresponding EP Application No. 10753706.0, dated Nov. 5, 2012.

* cited by examiner

*Primary Examiner* — Chih-Min Kam
(74) *Attorney, Agent, or Firm* — Sughrue Mion, PLLC

(57) ABSTRACT

The present invention provides a method for preparing a site-specific physiologically active polypeptide conjugate in a high yield by treating a physiologically active polypeptide with a non-peptidyl polymer in the presence of an alcohol at a specific pH, which can be desirably employed in the development of long acting formulations of various peptide drugs having high in-vivo activity and markedly prolonged in-blood half-life.

15 Claims, 33 Drawing Sheets

Lys12: CA-exendin-4-PEG (Lys12)
Lys27: CA-exendin-4-PEG (Lys27)

1 : His(1)-Ser(8)
2 : Asp(9)-Leu(14)
3 : Asp(16)-Gln(20)
4 : Asp(22)-(37)

NR: non-reducing condition
R: reducing condition

NR: non-reducing condition
R: reducing condition

NR: non-reducing condition
R: reducing condition

METHOD FOR PREPARING A SITE-SPECIFIC PHYSIOLOGICALLY ACTIVE POLYPEPTIDE CONJUGATE

CROSS-REFERENCE TO RELATED APPLICATIONS

This application is a National Stage application under 35 U.S.C. §371 of PCT/KR2010/001674 filed on Mar. 18, 2010, which claims priority from Korean patent application 10-2009-0023953 filed on Mar. 20, 2009, all of which are incorporated herein by reference.

FIELD OF THE INVENTION

The present invention relates to a method for preparing a site-specific physiologically active polypeptide conjugate, more particularly to a method for preparing said conjugate in a high yield by linking a physiologically active polypeptide with a non-peptidyl polymer.

BACKGROUND OF THE INVENTION

Peptides are easily denatured due to their low stability, degraded by in-vivo proteases, and excreted through the kidney due to their relatively small size. Accordingly, in order to maintain a specific concentration in the blood of a peptide drug in its active form, it is necessary to administer the peptide drug frequently to a patient. However, peptide drugs are usually administered in the form of injectable preparations, and such frequent administration cause severe discomfort for patients. To solve such problem, there have been developed a number of methods, e.g., a method for transferring the peptide drug through oropharyngeal or nasopharyngeal inhalation by increasing the permeation of the peptide drug through the biological membranes, a method for modifying a specific amino acid sequence which is sensitive to proteases (e.g., GLP-1 amino acid sequence for preventing loss of the titers by a dipeptidyl peptidase) in order to stabilize the peptide by inhibiting the degradation by the enzyme, and a method for chemically adding a non-peptidyl polymer with a high solubility, such as polyethylene glycol (PEG), on the surface of the peptide.

PEG, which has been used as one of non-peptidyl polymers, non-specifically binds to a specific site or multiple sites of a target peptide to attain the effect of increasing the molecular weight of the peptide, the resulting PEG-peptide resists the loss through the kidney and enzymatic hydrolysis, without causing any side-effects. For example, International Pat. Publication No. WO 2006/076471 describes sustaining the physiological activity of a B-type natriuretic peptide (BNP) used as congestive heart failure therapeutic agent by binding PEG thereto, and U.S. Pat. No. 6,924,264 describes increasing the in-vivo residence time of an exendin-4 drug by way of binding PEG to the lysine residue thereof.

These methods prolong the in-vivo residence time of a peptide drug by increasing the molecular weight of PEG, but as the molecular weight increases, the titer of the peptide drug becomes significantly reduced. In addition, the non-specific binding of PEG may shield the active domain of a physiologically active polypeptide to significantly lower the activity of the polypeptide.

Therefore, there is a need to develop an improved method for preparing a conjugate of a physiologically active polypeptide and a non-peptidyl polymer, in which the polymer is linked to the peptide in a site-specific manner that does not affect the polypeptide's activity.

The present inventors have completed the invention by confirming that a physiologically active polypeptide conjugate having a non-peptidyl polymer site-specifically linked can be prepared in a high yield by adjusting the pH and the alcohol content of the reaction medium.

SUMMARY OF THE INVENTION

Accordingly, it is an object of the present invention to provide a high-yield method for preparing a physiologically active polypeptide conjugate in which a non-peptidyl polymer site-specifically binds to a physiologically active polypeptide.

In accordance with one aspect of the present invention, there is provided a method for preparing a site-specific physiologically active polypeptide conjugate, comprising the steps of: i) subjecting to a reaction of a physiologically active polypeptide and a non-peptidyl polymer in a reaction medium which contains a specific amount of an alcohol and has a specific pH to enable the non-peptidyl polymer to bind to a target site of the physiologically active polypeptide; and ii) isolating and purifying the physiologically active polypeptide conjugate from the reaction mixture of step (i) by ion exchange chromatography using an alcohol.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Sequence Listing

Figure 9:
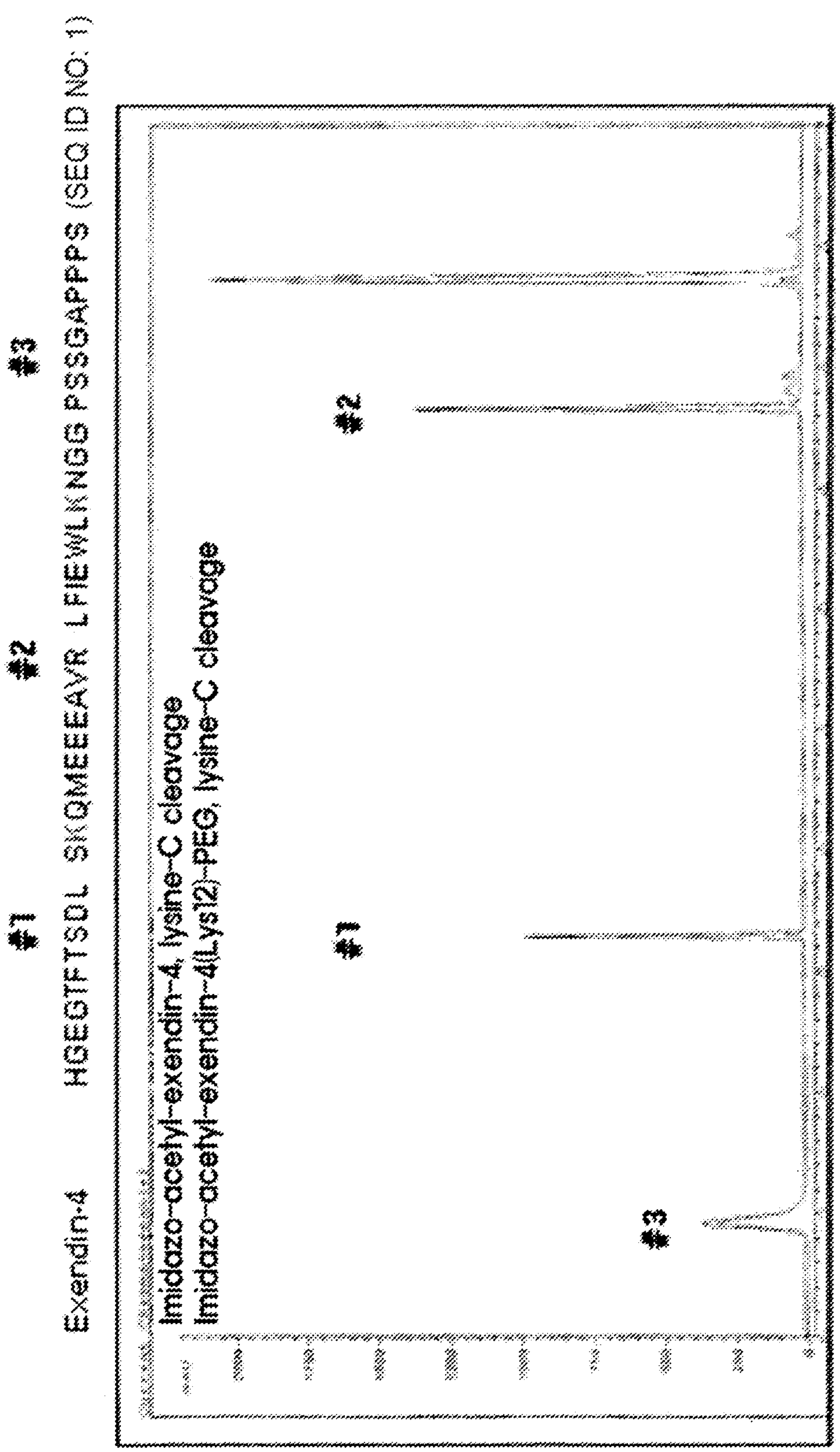
FIG. 9: an analysis profile of Lys12-pegylated isomers of CA-exendin-4 by peptide mapping.
Figure 10:
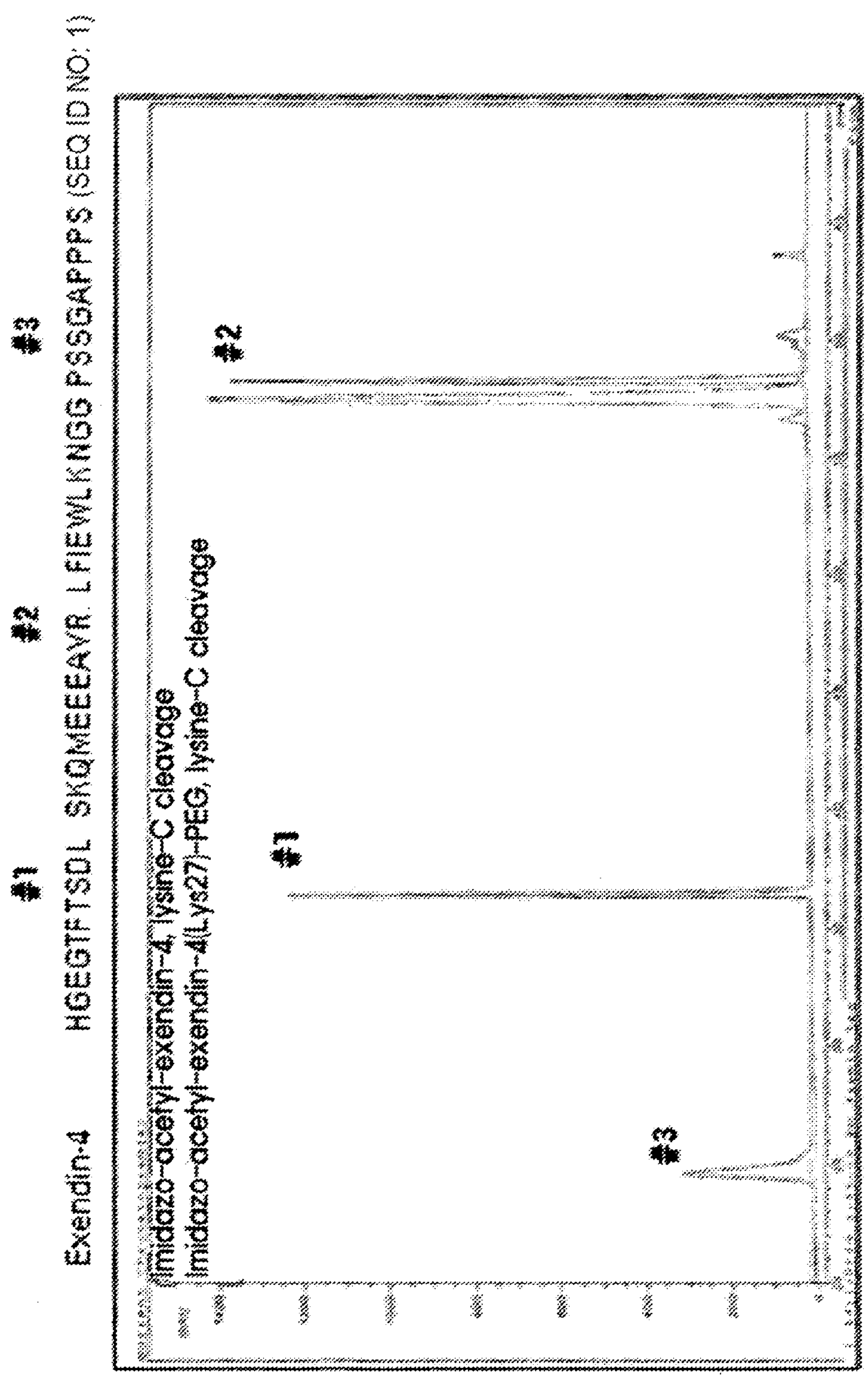
FIG. 10: an analysis profile of Lys27-pegylated isomers of CA-exendin-4 by peptide mapping.

The physiologically active polypeptide employed in the embodiments of the invention have the following sequence as shown in FIGS. 9-10, which is also reported in the sequence database such as the National Center for Biotechnology Information (NCBI).

SEQ ID NO: 1 : Exendin 4, Heloderma suspectum, NCBI Accession: AAB22006.1

Sequence: HGEGTFTSDLSKQMEEEAVR-LFIEWLKNGGPSSGAPPPS

Hereinafter, the present invention is described in detail.

The present invention provides a method for preparing a site-specific physiologically active polypeptide conjugate, comprising the steps of:

i) treating a physiologically active polypeptide with a non-peptidyl polymer in a reaction medium which contains a specific amount of an alcohol and has a specific pH to enable the non-peptidyl polymer bind to a target site of the physiologically active polypeptide; and ii) isolating and purifying the physiologically active polypeptide conjugate from the reaction mixture of step (i) by ion exchange chromatography using an alcohol.

A physiologically active polypeptide conjugate in accordance with the present invention refers to a substance in which a physiologically active polypeptide and a terminus of a non-peptidyl polymer are covalently linked to each other, and the present invention is characterized by linking a polypeptide with a polymer under a specific condition and isolating the resulting polypeptide conjugate having the polymer linked on a target site thereof.

The term "physiologically active polypeptide or peptide", as used herein, refers to a peptide which can exhibit a physiological activity in-vivo, e.g., may be selected from a group consisting of insulinotropic peptide, blood factor, digestive hormone, adrenocorticotropic hormone, thyroid hormone, intestinal hormone, cytokine, enzyme, growth factor, neuropeptide, hypophyseotropic hormone, hypophysiotropic hormone, anti-obesity peptide, anti-viral peptide, and non-native peptide derivatives retaining physiologically active property, but not limited thereto. More particularly, the physiologically active polypeptide or peptide is selected from the group consisting of erythropoietin, GM-CSF (granulocyte macrophage-colony stimulating factor), amylin, glucagon, insulin, somatostatin, PYY (peptide YY), NPY (neuropeptide Y), GLP-1, GLP-2, exendin-4, oxyntomodulin, ghrelin, angiotensin, bradykinin, calcitonin, corticotropin, eledoisin, gastrin, leptin, oxytocin, vasopressin, LH (luteinizing hormone), prolactin, FSH (follicle stimulating hormone), PTH (parathyroid hormone), secretin, sermorelin, hGH (human growth hormone), growth hormone-releasing peptide, G-CSFs (granulocyte colony stimulating factor), interferons, interleukins, prolactin-releasing peptide, orexin, thyroid-releasing peptide, cholecystokinin, gastrin-inhibiting peptide, calmodulin, gastrin-releasing peptide, motilin, vasoactive intestinal peptide, ANP (atrial natriuretic peptide), BNP (barin natriuretic peptide), CNP (C-type natriuretic peptide), neurokinin A, neuromedin, renin, endothelin, sarafotoxin peptide, carsomorphin peptide, dermorphin, dynorphin, endorphin, enkepalin, T cell factor, tumor necrosis factor, tumor necrosis factor receptor, urokinase receptor, tumor inhibitory factor, collagenase inhibitor, thymopoietin, thymulin, thymopentin, tymosin, thymic humoral factor, adrenomodullin, allatostatin, amyloid beta-protein fragment, antimicrobial peptide, antioxidant peptide, bombesin, osteocalcin, CART peptide, E-selectin, ICAM-1, VCAM-1, leucokine, kringle-5, laminin, inhibin, galanin, fibronectin, pancreastatin, and fuzeon. In addition, the physiologically active polypeptide includes a precursor, a derivative, a fragment, or a variant thereof.

The preferred physiologically active polypeptide used in the present invention is exendin, insulin, GLP-1, GLP-2, oxyntomodulin, ghrelin, angiotensin, bradykinin, calcitonin, or a derivative thereof. The derivative thereof may be prepared, e.g., by chemical substitution (e.g., alpha-methylation or alpha-hydroxylation), deletion (e.g., deamination or carbon deletion) or modification (e.g., N-methylation) of any groups on an amino acid residue, and particularly the preparation of the exendin derivative is described in detail in Korean Patent Application No. 2008-69234.

Meanwhile, the term "non-peptidyl polymer", as used herein, refers to a biocompatible polymer including two or more repeating units linked to each other by a covalent bond excluding a peptide bond.

The non-peptidyl polymer which can be used in the present invention may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof, and preferred is polyethylene glycol. A derivative thereof, which is known in the art or easily prepared based on the skill of the art, is also included within the scope of the present invention. The non-peptidyl polymer which can be used in the present invention functions to increase the molecular weight of a physiologically active polypeptide to prevent the loss of the conjugate through the kidney. Any non-peptidyl polymer, as long as it is resistant to in-vivo protease, can be used without any limitation. The molecular weight of the non-peptidyl polymer may be in the range of 0.5 to 100 kDa, preferably of 0.5 to 20 kDa, and the suitable molar ratio of the physiologically active polypeptide and the non-peptidyl polymer may be chosen in the range of from 1:1 to 1:50.

The non-peptidyl polymer used in the present invention has a reactive group at one end or at both ends. In case of the non-peptidyl polymer having a reactive group at both ends, it can bind to a physiologically active carrier and a protein drug which assist functioning as a long acting formulation.

The reactive group at one end or both ends of the non-peptidyl polymer is preferably selected from the group consisting of a reactive aldehyde group, a propionaldehyde group, a butyraldehyde group, a maleimide group and a succinimide group. Examples of the succinimide group include succinimidyl propionate, succinimidyl butanoate, hydroxy succinimidyl, succinimidyl carboxymethyl, or succinimidyl carbonate. In particular, when the non-peptidyl polymer has a reactive aldehyde group or a reactive succinimidyl group at one end, it is effective in linking at both ends with a physiologically active polypeptide and an immunoglobulin with minimal non-specific reactions. The aldehyde reactive group selectively binds to an N-terminus at a low pH, and can bind to a lysine residue to form an amine bond at a high pH, such as pH 9.0. In addition, the succinimidyl reactive group can form a stable amide bond with an amino terminus or lysine residue at pH 7.0~9.0.

Further, the reactive groups at both ends of the non-peptidyl polymer may be the same or different. When a polyethylene glycol having a reactive hydroxyl group at both ends thereof is used as the non-peptidyl polymer, the hydroxyl group may be activated into various reactive groups by known chemical reactions, or a commercially available polyethylene glycol having a modified reactive group may be used.

The step (i) of the present invention is to prepare a physiologically active polypeptide conjugate by site-specifically linking a non-peptidyl polymer with a physiologically active polypeptide in a suitable reaction medium.

The term "site-specific" or "site-specifically", as used herein, refers to the linking a non-peptidyl polymer onto a specific target amino acid site of a physiologically active polypeptide, preferably an amine of the lysine residue or N-terminus. The site-specific linking or bond may prevent the formation of incidental conjugates in which the non-peptidyl polymer is linked to a physiologically important amino acid residue. For example, when a non-peptidyl polymer binds to the N-terminus of exendin-4, in-vitro activity of the exendin-4 became reduced, but when a non-peptidyl polymer binds to a lysine residue, in-vitro activity was maintained. In particular, when a non-peptidyl polymer binds to $27^{th}$ lysine residue rather than $12^{th}$ lysine residue, much higher in-vitro activity was observed (See Example 10 and Table 2).

The present inventors have found that the presence of an alcohol in a reaction medium and the pH of the reaction medium in step (i) are critical factors for a site-specific bond of a non-peptidyl polymer and a physiologically active polypeptide. Accordingly, in the step (i) of the present invention, a non-peptidyl polymer becomes linked to a specific site of a physiologically active polypeptide, using a reaction medium containing a specific content of an alcohol and having a specific pH.

In a specific embodiment of the present invention, the ratio of a specific positional isomer of the polypeptide conjugate can be varied based on the pH of the reaction medium, or based on the concentration (%) of an alcohol at same pH. It is therefore possible to link a non-peptidyl polymer to a desired amino acid of a physiologically active polypeptide in a site-specific manner.

That is, the step (i) of the present invention is carried out at a specific pH to enable the non-peptidyl polymer to bind to a desired (or target) site, i.e., that dose not affect the polypeptide's activity. The pH range may depend on the types of physiologically active polypeptide. For instance, in case of an insulinotropic peptide (e.g., exendin-4), an isomer in which the polymer is linked to the $12^{th}$ lysine was highly observed at low pH of the reaction medium, whereas an isomer in which the polymer is linked to the $27^{th}$ lysine which does not affect the insulinotropic activity was highly observed at high pH of the reaction medium (See Example 3 and FIG. 3). Accordingly, the step (i) is preferably carried out at pH 7.5 to 9.0 so that the non-peptidyl polymer is selectively coupled to the $27^{th}$ lysine.

Further, the step (i) of the present invention is carried out in a reaction medium containing an alcohol so that a non-peptidyl polymer can bind to a site that does not affect the polypeptide's activity. Examples of the alcohol include primary, secondary, and tertiary alcohol, preferably an alcohol having a carbon number of one to ten, more preferably ethanol or isopropanol. In case of an insulinotropic peptide (e.g., exendin-4), an alcohol may be present in the reaction medium, in an amount ranging from 0.1% to 100% by volume, preferably from 25% to 90%, more preferably from 35% to 60%, based on the total volume of the reaction medium, in order to enable a non-peptidyl polymer to bind to the $27^{th}$ lysine that does not affect the insulinotropic activity.

In an embodiment of the present invention, when a physiologically active polypeptide is exendin-4 (SEQ ID NO: 1) or a derivative thereof, the pH employed in step (i) may be 7.0 to 10.0 in order to enhance the binding ratio of a non-peptidyl polymer to Lys27. In other embodiment of the present invention, when a physiologically active polypeptide is calcitonin, the pH employed in step (i) may be 4.0 to 6.0 in order to enhance the binding ratio of a non-peptidyl polymer to N-terminus. In another embodiment of the present invention, when a physiologically active polypeptide is oxyntomodulin (SEQ ID NO: 2) or a derivative thereof, the pH employed in step (i) may be 7.0 to 10.0 in order to enhance the binding ratio of a non-peptidyl polymer to Lys27 or Lys30. In another embodiment of the present invention, when a physiologically active polypeptide is human insulin or a derivative thereof, the pH employed in step (i) may be 4.0 to 6.0 in order to enhance the binding ratio of a non-peptidyl polymer to Phe1 ($1^{st}$ phenylalanine) N-terminus in human insulin B chain (SEQ ID NO:4). In another embodiment of the present invention, when a physiologically active polypeptide is human insulin or a derivative thereof, the pH employed in step (i) may be 7.0 to 10.0 in order to enhance the binding ratio of a non-peptidyl polymer to Glyl ($1^{st}$ glycine) N-terminus in human insulin A chain (SEQ ID NO: 3) , or to Lys29 ($29^{th}$ lysine) in B chain (SEQ ID NO: 4). In another embodiment of the present invention, when a physiologically active polypeptide is GLP-1 (SEQ ID NO: 5) or a derivative thereof, the pH employed in step (i) may be 7.0 to 10.0 in order to enhance the binding ratio of a non-peptidyl polymer to Lys34. In another embodiment of the present invention, when a physiologically active polypeptide is GLP-2 (SEQ ID NO: 6) or a derivative thereof, the pH employed in step (i) may be 7.0 to 10.0 in order to enhance the binding ratio of a non-peptidyl polymer to Lys30.

Accordingly, the preferred site-specific physiologically active polypeptide conjugate of the present invention is an exendin-4 conjugate in which PEG is linked to Lys27, a calcitonin conjugate in which PEG is linked to N-terminus, an oxyntomodulin (SEQ ID NO: 2) conjugate or an analogue thereof in which PEG is linked to Lys27 or Lys30, a human insulin (e.g., insulin A chain of SEQ ID NO: 3 or insulin B chain of SEQ ID NO: 4) conjugate or an analogue thereof in which PEG is linked to Phel N-terminus in B chain (SEQ ID NO: 4), Glyl N-terminus in A chain (SEQ ID NO: 3), or to Lys29 in B chain (SEQ ID NO: 4), or a GLP-1 (SEQ ID NO: 5) or GLP-2 (SEQ ID NO: 6) conjugate in which PEG is linked to Lys34 or Lys30.

In a preferred aspect of the present invention, a peptide derivative (or analogue) may be used to facilitate a site-specific bond between a non-peptidyl polymer and a physiologically active polypeptide. The derivative is a peptide having any of other non-target amino acid sites deleted or protected in order to prevent undesired linking. For example, in case of a insulinotropic peptide such as an exendin, various exendin derivatives may be used, such as Des-amino-histidyl (DA)-exendin-4 of formula (I), Beta-hydroxy-imidazopropionyl (HY)-exendin-4 of formula (II), Imidazoacetyl(CA)-exendin-4 of formula (III), and Dimethyl-histidyl(DM)-exendin-4 of formula (IV), which are prepared using the methods where an alpha amine group of N-terminal amino acid, histidine is deleted, the N-terminal amine group is substituted with hydroxyl group, the N-terminal alpha amine group of histidine is modified with two methyl groups, or an alpha carbon of N-terminal histidine and an amine group bound thereto are deleted to leave an imidazoacetyl group, but not limited thereto. The structures of such exemplary exendin derivatives and methods of preparation thereof are described in Korean Unexamined Patent Publication No. 2009-0008151, which is included within the scope of the present invention by references.

Formula I

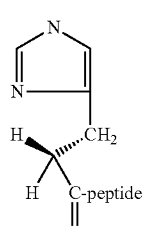

Formula II

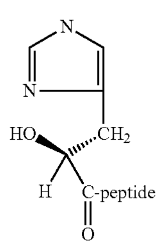

-continued

Formula III

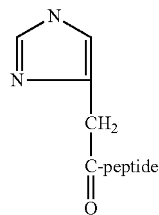

Formula IV

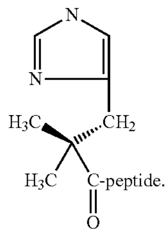

Similarly, oxyntomodulin, GLP-1 and GLP-2 having a histidine as $1^{st}$ amino acid may also be used as a derivative having any structure selected from Formulas (I) to (IV).

In a particular embodiment of the present invention, the present inventors have investigated the effects of the pH and the content of an alcohol (%) of the reaction medium on the site-specific binding aspect of the non-peptidyl polymer, and confirmed that the ratio of the insulinotropic peptide conjugates having the polymer linked to $12^{th}$ lysine/$27^{th}$ lysine is varied depending on the change of pH and amount of ethanol or isopropanol, in particular. In particular, a more preferable isomer having the non-peptidyl polymer bound to the $27^{th}$ lysine residue was largely obtained, when 35% to 55%, preferably about 45% of ethanol or isopropanol is used at pH 7.5.

After enhancing the ratio of the desired non-peptidyl polymer-physiologically active polypeptide conjugate by adjusting into a specific pH and an alcohol content in step (i), the desired conjugate can be isolated and purified by ion exchange chromatography using an alcohol in step (ii).

The alcohol used in step (ii) is present in a purification solution, and its specific examples are same as defined in step (i). However, the alcohol of step (i) was employed for the purpose of increasing the polypeptide's reactivity and site-specificity by modification of secondary or tertiary structure thereof, whereas the alcohol of step (ii) was employed for the purpose of facilitating the high-throughput isolation and purification of the site-specific physiologically active polypeptide conjugate by reduction of non-specific bond between ion-exchange column and the conjugate. The isolation and purification may be carried out by using various methods known to a person skilled in the art, preferably by ion exchange chromatography, more preferably by high pressure ion exchange chromatography.

Meanwhile, in order to facilitate the isolation and purification of positional isomer, the ion exchange chromatography may be carried out at a specific pH. The pH was suitably adjusted to increase the conjugate's site-specificity in step (i), whereas it was re-adjusted to attach the conjugate to and to detach it from the ion exchange column in a purification solution containing an alcohol in step (ii). The suitable pH employed in step (ii) may be in the range from about 2.0 to about 6.0.

Furthermore, the physiologically active polypeptide of the present invention may further be linked with a physiologically active carrier. In this case, the non-peptidyl polymer should be a non-peptidyl polymer with both ends in order to bind with the physiologically active carrier. That is, a physiologically active carrier covalently binds to an end of the non-peptidyl polymer which is not covalently linked with the physiologically active polypeptide, and thus it can be prepared a conjugate in which both ends of non-peptidyl polymer are linked with the physiologically active polypeptide and the physiologically active carrier.

As described above, the physiologically active polypeptide conjugate prepared in step (ii) may further bind with a physiologically active carrier, and the resulting polypeptide-polymer-carrier conjugate shows completely different activities compared to the polypeptide-polymer conjugate, i.e., the outstanding physiological activities such as excellent prolonged duration of pharmacological effects of a physiologically active polypeptide, targeting to a specific site such as a lesion to be treated, or induction of necrosis.

The term “physiologically active carrier”, as used herein, refers to a physiologically active substance showing additional activities distinct to the native polypeptide's physiological activity, which can sustain the polypeptide's physiological activities such as the pharmacological effects, or induce targeting to a specific site or necrosis, by binding to a non-peptidyl polypeptide together with a physiologically active polypeptide.

The physiologically active carrier used in the present invention includes a substance having afore-mentioned activities without any limitation, e.g., albumin, immunoglobulin Fc region, transferrin, aptamer, toxin, collagen, dextran, polysaccharides, fatty acids, fibrinogen, and the like. Preferably, the physiologically active carrier may be selected from an albumin, an immunoglobulin Fc region, and a transferrrin, more preferably an immunoglobulin Fc region.

The immunoglobulin Fc region of the present invention refers to the heavy chain constant region 2 (CH2) and the heavy chain constant region 3 (CH3) of an immunoglobulin, excluding the variable regions of the heavy and light chains, the heavy chain constant region 1 (CH1) and the light chain constant region 1 (CL1). It may further include a hinge region at the heavy chain constant region. Also, the immunoglobulin Fc region of the present invention may be a extended form containing a part or all of the Fc region including the heavy chain constant region 1 (CH1) and/or the light chain constant region 1 (CL1), except for the variable regions of the heavy and light chains, as long as it has a physiological function substantially similar to or better than the native immunoglobulin Fc, and may include immunoglobulin Fc regions modified by phosphorylation, sulfation, acrylation, glycosylation, methylation, farnesylation, acetylation, amidation, and the like. The range of immunoglobulin Fc, method for preparation thereof, and method for covalently linking an immunoglobulin Fc to a non-peptidyl polymer-physiologically active polypeptide conjugate are disclosed in Korean Patent Nos. 775343, 725314, 725315, and 824505, which are included within the scope of the present invention by references.

In accordance with the method of the present invention, a desired polypeptide conjugate having an excellent physiological activity can be prepared in a high yield by site-specifically linking a non-peptidyl polymer to a specific amino acid of a physiologically active polypeptide, while minimizing the formation of additional conjugates.

The following Examples are intended to further illustrate the present invention without limiting its scope.

Example 1

Preparation and Isolation of Pegylated DA-Exendin-4 (Lys27) Conjugate

<1-1> Preparation of Pegylated DA-Exendin-4 (Lys27) Conjugate

In order to prepare a pegylated peptide conjugate by covalently linking Lys in the peptide with the PEG, des-amino-histidyl-exendin-4 (DA-exendin-4, AP, U.S.) and 3.4K PropionALD(2) PEG (PEG having two propionaldehyde groups, IDB Inc., Korea) was subjected to a reaction at 4° C. for 12 hours at a molar ratio of 1:30, with a peptide concentration of 3 mg/mL. At this time, 100 mM HEPES buffer (pH 7.5) containing 45% isopropanol was used as a reaction medium, and 20 mM $NaCNBH_3$ as a reducing agent was added thereto.

<1-2> Isolation of Positional Isomer

A mono-pegylated peptide was primarily purified from the reaction mixture of Example <1-1> by using an SOURCE Q ion exchange chromatography (XK 16 mL, GE healthcare, Korea) under the following condition, and positional isomers were isolated by using an SOURCE S ion exchange chromatography (XK 16 mL, GE healthcare, Korea) under the following condition. In this process, ethanol was used to facilitate the isolation of isomers, by including it in a purification solution. The pegylated sites were confirmed from eluted peaks by peptide mapping method.

Column: SOURCE Q

Flow rate: 2.0 mL/min

Figure 1:
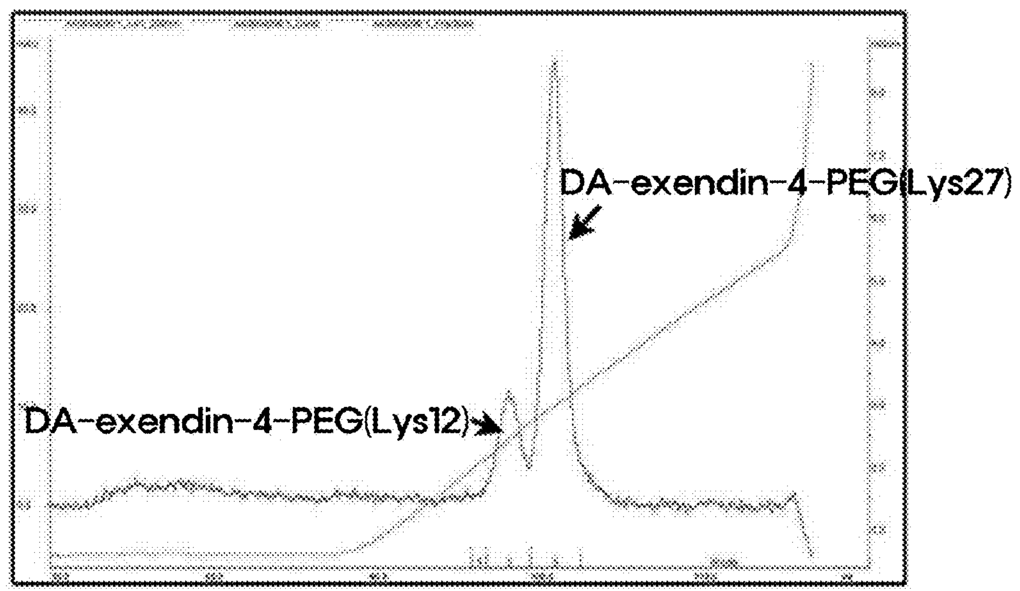
FIG. 1: a purification profile of positional isomers of DA-exendin-4-PEG using SOURCE S column.

Eluting solution: A (20 mM Tris, pH 8.5) and B (A+0.5M NaCl); Gradient A 0→40%, 80 min Column: SOURCE S Flow rate: 2.0 mL/min Eluting solution: A (20 mM citric acid, pH 3.0+45% ethanol) and B (A+45% ethanol+0.5M KCl); Gradient A 0→100%, 45 min From the analysis of the purification profile of positional isomers, it was found that a peak for Lys12-pegylated DA-exendin-4 was eluted earlier, and then a Lys27-pegylated peak was eluted in the last portion (FIG. 1).

Example 2

Preparation and Isolation of Pegylated CA-Exendin-4 (Lys27) Conjugate

Figure 2:
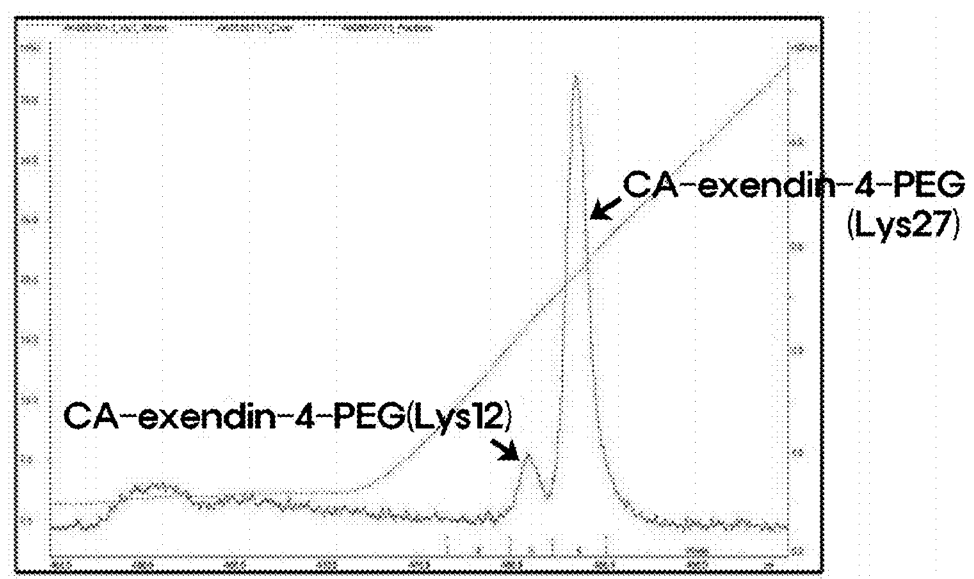
FIG. 2: a purification profile of positional isomers of CA-exendin-4-PEG using SOURCE S column.

The procedure of Example 1 was repeated except for using imidazo-acetyl-exendin-4 (CA-exendin-4, Bachem, U.S.) instead of DA-exendin-4 in Example 1 to obtain the pegylated CA-exendin-4 (Lys27) conjugate. From the analysis of the purification profile of positional isomers, it was found that a peak for Lys12-pegylated CA-exendin-4 was eluted earlier, and then a Lys27-pegylated peak was eluted in the last portion (FIG. 2).

Example 3

Figure 3:
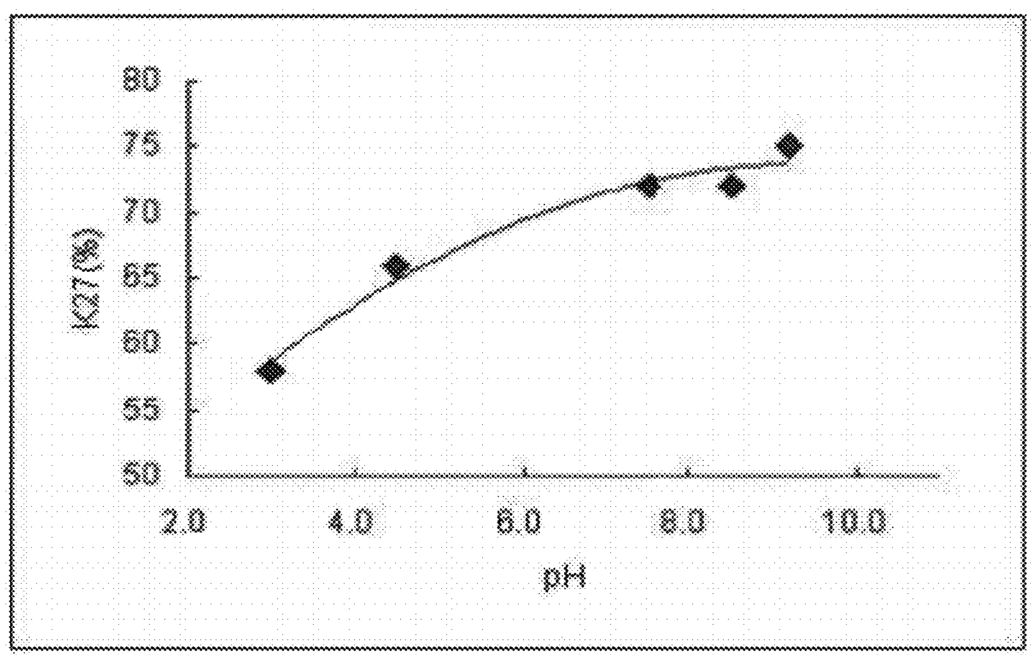
FIG. 3: a graph showing Lys27-pegylated isomers obtained when CA-exendin-4 is pegylated at varying pH.

Change in Ratio of Pegylated CA-Exendin-4 (Lys27) Conjugate According to pH of Reaction Medium To investigate the change in ratio of a polypeptide pegylated at a specific site by pH, CA-exendin-4 and 3.4K PropionALD(2) PEG were subjected to pegylation by reacting the peptide and the PEG at 4° C. for 12 hours at a molar ratio of 1:30, with a peptide concentration of 3 mg/mL. At this time, 100 mM citric acid (pH 3.0), 100 mM NaOAc (pH 4.5), 100 mM Na—P (pH 7.5), 100 mM Na—P (pH 8.5), 100 mM HEPES (pH 8.0), and 100 mM Na-Borate (pH 9.2) buffers were used as a reaction medium, respectively, and 20 mM $NaCNBH_3$ as a reducing agent was added thereto. Each reaction mixture was purified by the method described in Example 1, followed by analyzing the ratio of the Lys27-pegylated conjugate. As shown in FIG. 3, the ratio of the Lys27-pegylated conjugate was increased based on the increase in pH, and the optimum pH was confirmed to be 7.0 to 10.0.

Example 4

Figure 4:
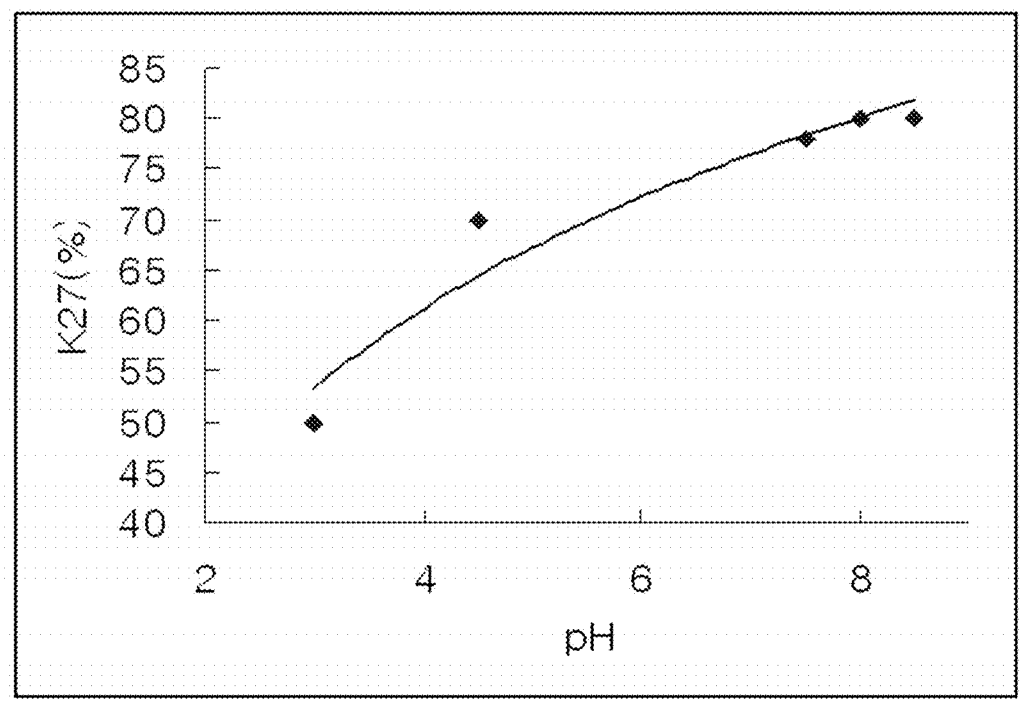
FIG. 4: a graph showing Lys27-pegylated isomers obtained when CA-exendin-4 is pegylated at varying pH and in 45% EtOH.

Change in Ratio of Pegylated CA-Exendin-4 (Lys27) Conjugate According to pH of Reaction Medium Containing Ethanol To investigate the change in the ratio of a polypeptide pegylated at a specific site by ethanol and pH, CA-exendin-4 and 3.4K PropionALD(2) PEG were subjected to pegylation by reacting the peptide and the PEG at 4° C. for 12 hours at a molar ratio of 1:30, with a peptide concentration of 3 mg/mL. At this time, 100 mM citric acid (pH 3.0)/45% ethanol, 100 mM NaOAc (pH 4.5)/45% ethanol, 100 mM Na—P (pH 7.5)/45% ethanol, 100 mM HEPES (pH 8.0)/45% ethanol, and 100 mM Na—P (pH 8.5)/45% ethanol buffers were used as a reaction medium, respectively, and 20 mM $NaCNBH_3$ as a reducing agent was added thereto. Each reaction mixture was purified by the method described in Example 1, followed by analyzing the ratio of the Lys27-pegylated conjugate. As shown in FIG. 4, the ratio of the Lys27-pegylated conjugate was increased based on the increase in pH in a 45% EtOH-containing reaction medium, and the optimum pH was confirmed to be 7.0 to 9.0.

Example 5

Figure 5:
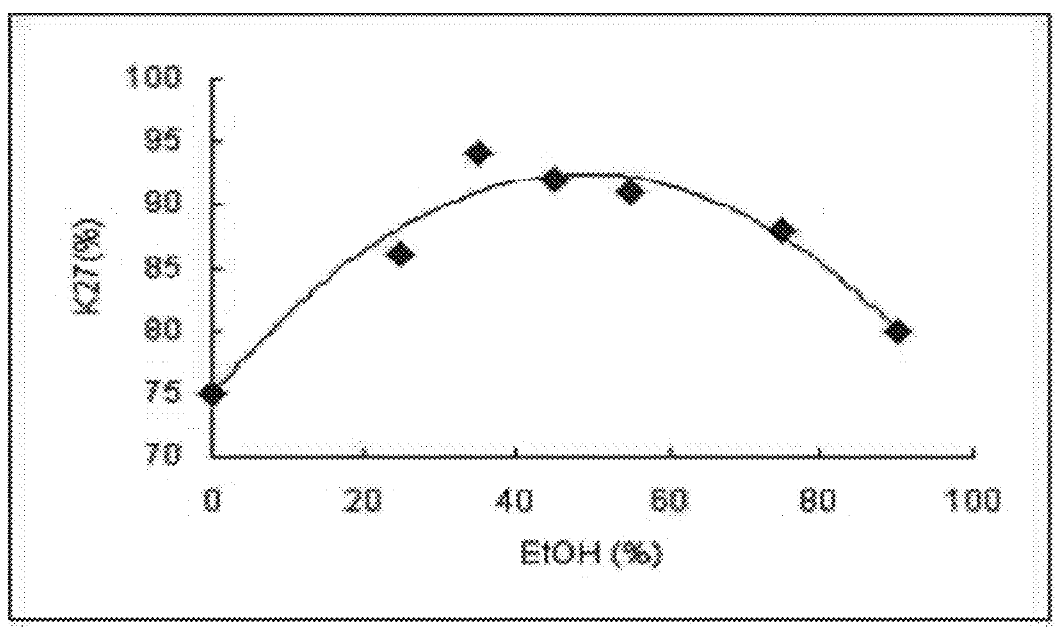
FIG. 5: a graph showing Lys27-pegylated isomers obtained when CA-exendin-4 is pegylated at pH 7.5 and in a varying amount (%) of ethanol.

Change in Ratio of Pegylated CA-Exendin-4 (Lys27) Conjugate According to Ethanol Concentration in Reaction Medium To investigate the change in ratio of a polypeptide pegylated at a specific site by ethanol concentration in the reaction medium, CA-exendin-4 and 3.4K PropionALD(2) PEG were subjected to pegylation by reacting the peptide and the PEG in at 4° C. for 12 hours at a molar ratio of 1:30, with a peptide concentration of 3 mg/mL. At this time, 100 mM HEPES (pH 7.5)/0% ethanol, 100 mM HEPES (pH 7.5)/25% ethanol, 100 mM HEPES (pH 7.5)/35% ethanol, 100 mM HEPES (pH 7.5)/45% ethanol, 100 mM HEPES (pH 7.5)/55% ethanol, 100 mM HEPES (pH 7.5)/75% ethanol and 100 mM HEPES (pH 7.5)/90% ethanol buffers were used as a reaction medium, respectively, and 20 mM $NaCNBH_3$ as a reducing agent was added thereto. Each reaction mixture was purified by the method described in Example 1, followed by analyzing the ratio of the Lys27-pegylated conjugate. As shown in FIG. 5, the ratio of the Lys27-pegylated conjugate was increased until the amount of ethanol reaches about 50%, whereas decreased in more than 50% of ethanol, and the optimum amount of ethanol was confirmed to be 35% to 60%.

Example 6

Figure 6:
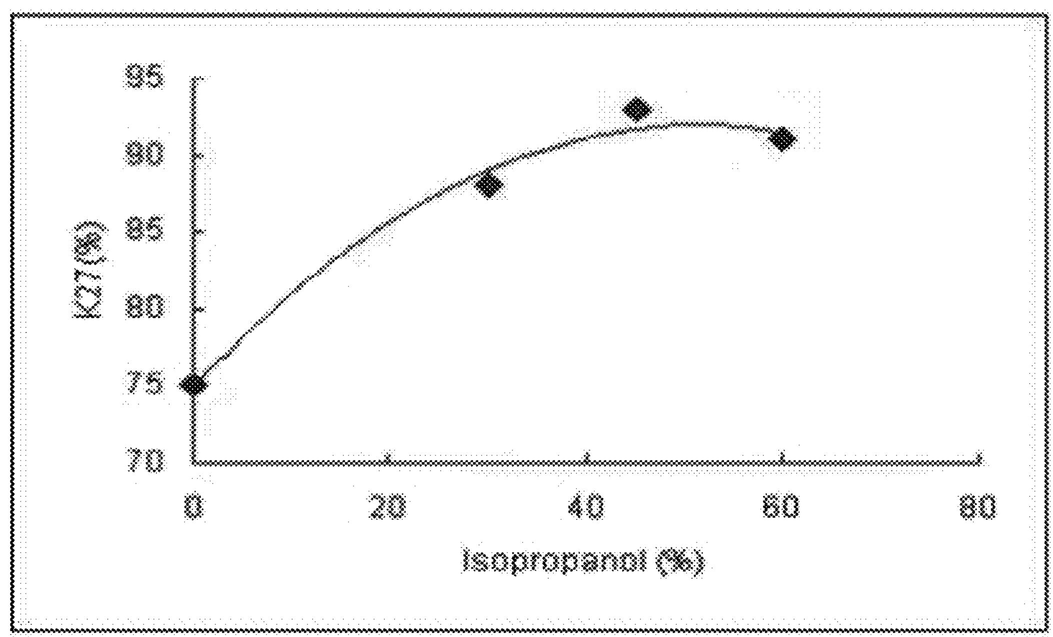
FIG. 6: a graph showing Lys27-pegylated isomers obtained when CA-exendin-4 is pegylated at pH 7.5 and in a varying amount (%) of isopropanol.

Change in Ratio of Pegylated CA-Exendin-4 (Lys27) Conjugate According to Isopropanol Concentration in Reaction Medium To investigate the change in ratio of a polypeptide pegylated at a specific site by the use of isopropanol instead of ethanol, in the reaction medium, CA-exendin-4 and 3.4K PropionALD(2) PEG were subjected to pegylation by reacting the peptide and the PEG at 4° C. for 12 hours at a molar ratio of 1:30, with a peptide concentration of 3 mg/mL. At this time, 100 mM HEPES (pH 7.5)/0% isopropanol, 100 mM HEPES (pH 7.5)/30% isopropanol, 100 mM HEPES (pH 7.5)/45% isopropanol, and 100 mM HEPES (pH 7.5)/60% isopropanol buffers were used as a reaction medium, respectively, and 20 mM $NaCNBH_3$ as a reducing agent was added thereto. Each reaction mixture was purified by the method described in Example 1, followed by analyzing the ratio of the Lys27-pegylated conjugate. As shown in FIG. 6, the ratio of the Lys27-pegylated conjugate was increased until the amount of ethanol reaches about 50%, whereas decreased in more than 50% of ethanol, and the optimum amount of ethanol was confirmed to be 35% to 60%.

Example 7

Preparation of a Conjugate of CA-Exendin-4 (Lys27)-PEG and Immunoglobulin Fc CA-exendin-4 (Lys27)-PEG conjugate was coupled with an immunoglobulin Fc fragment (Hanmi Pharm. Co. Ltd., Korea), by subjecting to a reaction of the conjugate and the fragment at 4° C. for 16 hours at a molar ratio of 1:8, with a peptide concentration of 20 mg/mL. At this time, 100 mM K-P buffer (pH 6.0) was used as a reaction medium, and 20 mM NaCNBH3 as a reducing agent was added thereto. After the coupling reaction, the two-step purification was performed using SOURCE phe and SOURCE Q columns, under following conditions.

Column: SOURCE Phe (XK 16 mL, GE healthcare)

Flow rate: 2.0 mL/min

Eluting solution: A (20 mM Tris, pH 7.5) and B (A+1.5M NaCl); Gradient A 0→40%, 80 min Column: SOURCE Q (XK 16 mL, GE healthcare)

Flow rate: 2.0 mL/min

Figure 7:
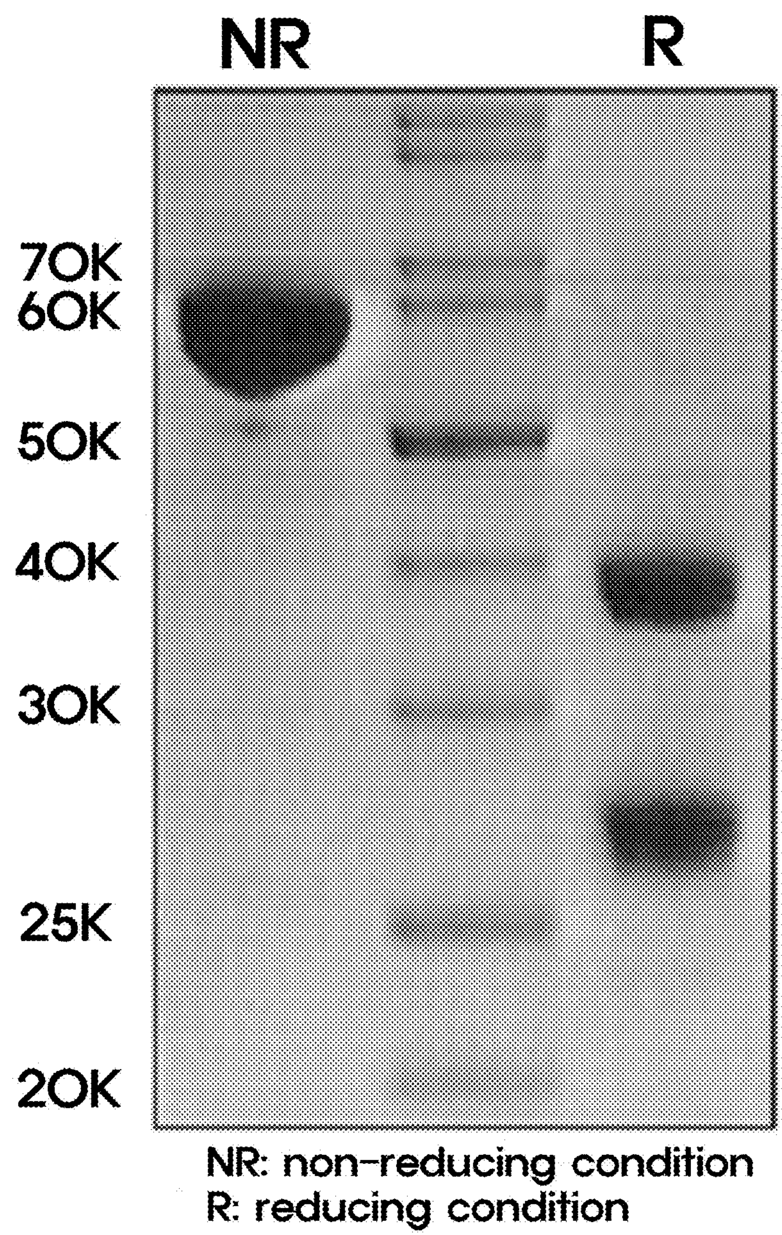
FIG. 7: an SDS-PAGE analysis of CA-exendin-PEG-immunoglobulin Fc.

Eluting solution: A (20 mM Tris, pH 7.5) and B (A+1M NaCl); Gradient A 0→40%, 80 min The conjugate prepared above was analyzed using SDS-PAGE. As shown in FIG. 7, a single band with 60K was observed under a non-reducing condition, whereas two bands with 35K and 25K were observed under a reducing condition.

Example 8

Identification of Pegylated Site of CA-Exendin-4 (Lys27)-PEG Conjugate

To identify the binding site of PEG to CA-exendin-4, the CA-exendin-4 (Lys27)-PEG conjugates were digested with a protease enzyme, lysine-C, and the analyzed using a reverse chromatography.

Figure 8:
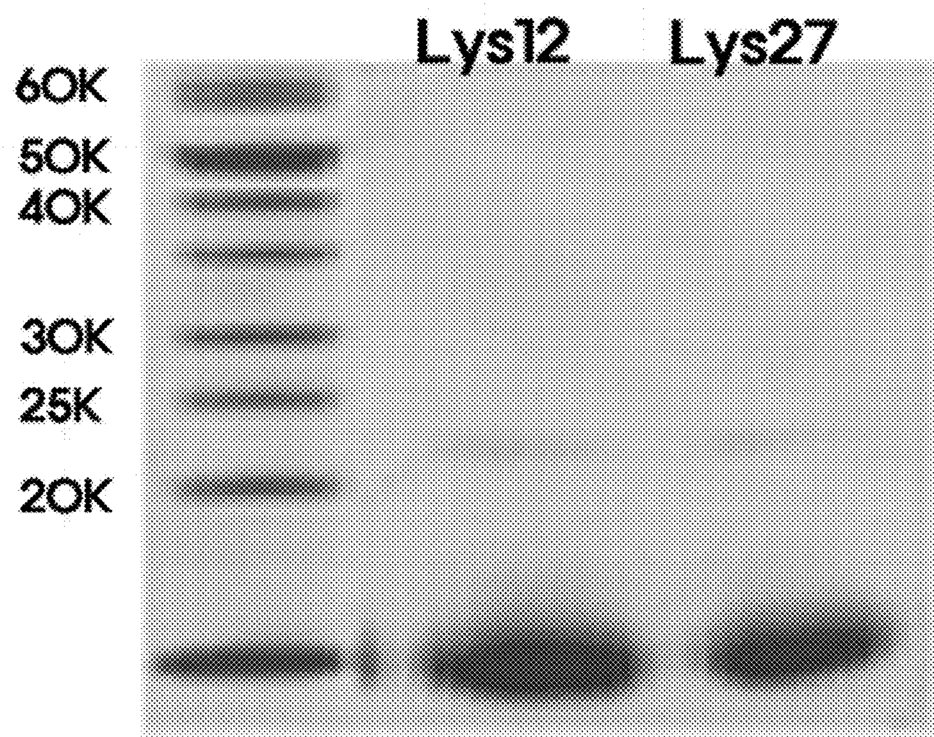
FIG. 8: an SDS-PAGE analysis of CA-exendin-PEG Lys12 and Lys27.

Specifically, CA-exendin-4-PEG isomers were analyzed by SDS-PAGE (FIG. 8), and then a purified CA-exendin-4-PEG conjugate and CA-exendin-4 were dissolved in triethylamine-hydrochloric acid buffer (10 mmol/L; pH 7.5), 10 µL of enzyme (0.1 mg/mL) was added thereto, and reacted at 37° C. for 4 hours. After the reaction was terminated, the reaction mixture was analyzed by a reverse chromatography (HPLC (Agilent), Jupiter C18 (Phenomenex)). The analysis results are shown in FIGS. 9 and 10. A Lys12-pegylated CA-exendin-4 isomer was confirmed by simultaneous disappearance of #1 and #2 as shown in FIG. 9, and a Lys27-pegylated CA-exendin-4 isomer was confirmed by simultaneous disappearance of #2 and #3 as shown in FIG. 10.

Example 9

Identification of Pegylation Yield by Isopropanol Concentration on N-Terminal Pegylation To pegylate methoxy polyethylene glycol 5K ALD (NOF Inc., Japan) to the N-terminal of calcitonin salmon (Bachem, U.S.), a calcitonin salmon and PEG was subjected to pegylation by reacting the peptide and the PEG at 4° C. for 1 hour at a molar ratio of 1:1, with a peptide concentration of 1 mg/mL. At this time, 100 mM NaAc pH 5.2/0% isopropanol, 100 mM NaAc pH 5.2/45% isopropanol buffers were used as a reaction medium, respectively, and 20 mM $NaCNBH_3$ as a reducing agent was added thereto. A mono-pegylated peptide was purified from each of the reaction mixtures by SOURCE S column (XK 16 mL, GE healthcare, Korea) under the following condition. The results are shown in Table 1 below.

Column: SOURCE S

Flow rate: 2.5 mL/min

Eluting solution: A (20 mM Acetate, pH 5.2) and B (A+1M NaCl); Gradient A 0→40%, 60 min

TABLE 1

| Reaction buffer solution | Yield of mono-pegylated calcitonin-5K (%) |
|---|---|
| 0.1M NaAc pH 5.2 | 36 |
| 0.1M NaAc pH 5.2/45% IPA | 51.3 |

As shown in Table 1, the yield of a pegylated calcitonin became increased by addition of iospropanol.

Example 10

Measurement of In-Vitro Activity of Exendin-4 by Pegylation and Pegylated Site To measure the efficacy of long acting preparation of exendin-4 by pegylation and pegylation site, a method for measuring the in-vitro activity was used. The measurement of in-vitro activity of GLP-1 is a method for measuring whether cAMP's in the cell was increased after treatment of GLP-1 to CHO cell lines to which GLP-1 receptors was cloned.

Specifically, CHO/GLP-1R, a cell line in which GLP-1 is cloned, was treated with GLP-1, exendin-4 and test materials described in Table 1 at varying concentrations. The occurrence of cAMP's was measured, and hence EC50 values were compared to each other. As a control, commercially available Byetta (Eli Lilly) was used. The in-vitro activities (%) according to treatment of test materials were shown in Table 2.

TABLE 2

| Test material | In-vitro activity (%) |
|---|---|
| Byetta | 100 |
| CA-exendin-4 | 77 |
| CA-exendin-4-PEG (Lys12) | 2.1 |
| CA-exendin-4-PEG (Lys27) | 8.5 |

As shown in Table 2, the physiological activity of the peptide was relatively less affected when PEG is modified at Lys27, compared to Lys12.

Example 11

Preparation and Isolation of Pegylated Oxyntomodulin (Lys30) Conjugate

<11-1> Preparation of Pegylated Oxyntomodulin Conjugate (Lys30)

To prepare a pegylated oxyntomodulin conjugate, 3.4K PropionALD(2) PEG and oxyntomodulin (Anygen, Korea) were subjected to pegylation by reacting the peptide and the PEG at 4° C. for 4.5 hours at a molar ratio of 1:15, with a peptide concentration of 3 mg/mL. At this time, 100 mM Na-Borate buffer (pH 9.0) containing 45% isopropanol was used as a reaction medium, and 20 mM $NaCNBH_3$ as a reducing agent was added thereto.

<11-2> Isolation of Positional Isomer

Figure 11:
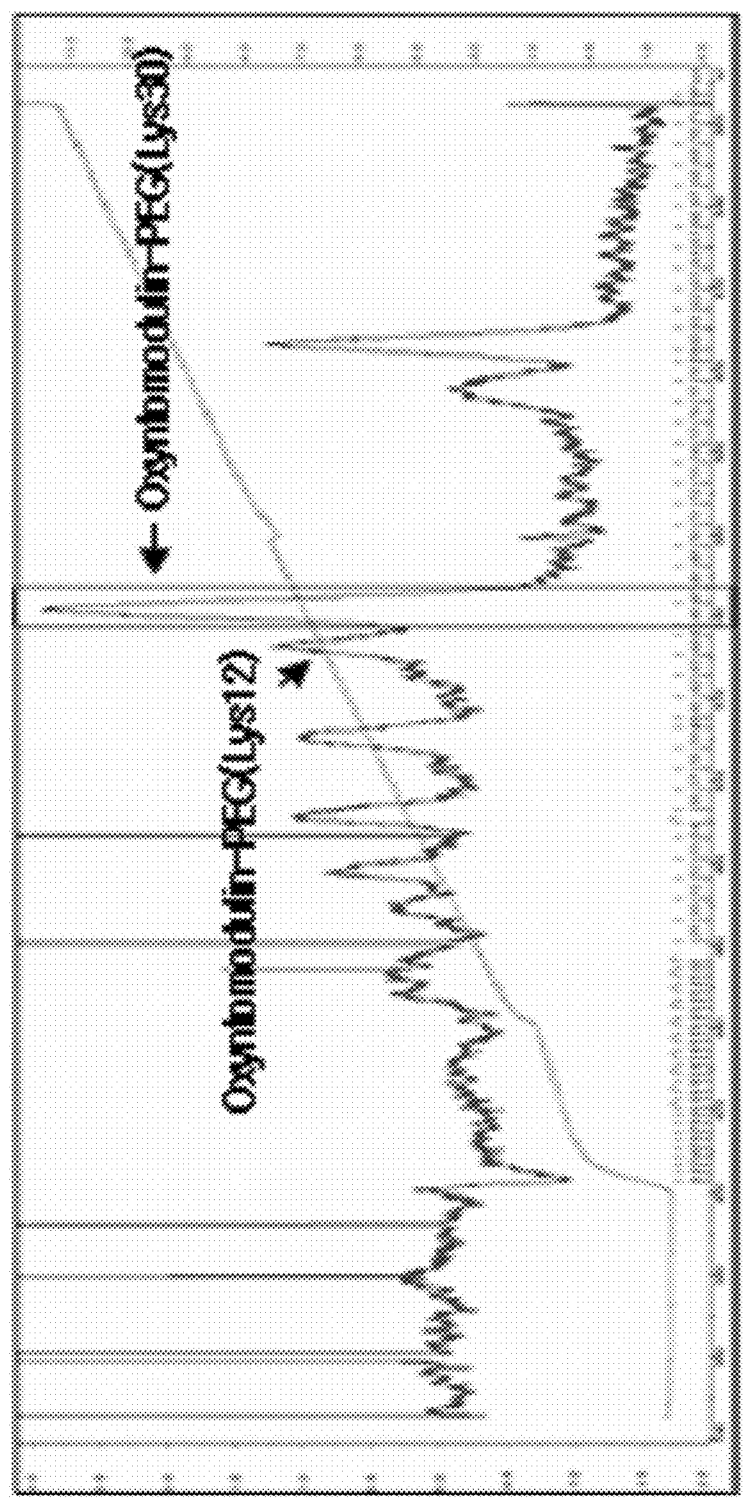
FIG. 11: a purification profile of positional isomers of oxyntomodulin-PEG using SOURCE S column.

Lys30-pegylated Positional isomers were purified from the reaction mixture by using SOURCE 15S column (XK 16 mL, Amersham Bioscience). In this process, ethanol was used in the purification solution to facilitate the isolation of isomers (FIG. 11).

Column: SOURCE S

Flow rate: 2.0 mL/min

Eluting solution: A (20 mM Na-citrate, pH 3.0+45% ethanol) and B (A+1M KCl); Gradient A 0→3%, 1 min, Gradient B 0→40%, 222 min

Example 12

Preparation and Isolation of Pegylated Imidazo-Acetyl Oxyntomodulin (Lys30) Conjugate The procedure of Example 11 was repeated except for using imidazo-acetyl-oxyntomodulin (Anygen, Korea) instead of oxyntomodulin and using 100 mM HEPES buffer (pH 7.5) containing 45% isoparopanol in Example 11 to obtain the pegylated imidazo-acetyl oxyntomodulin (Lys30) conjugate.

Figure 12:
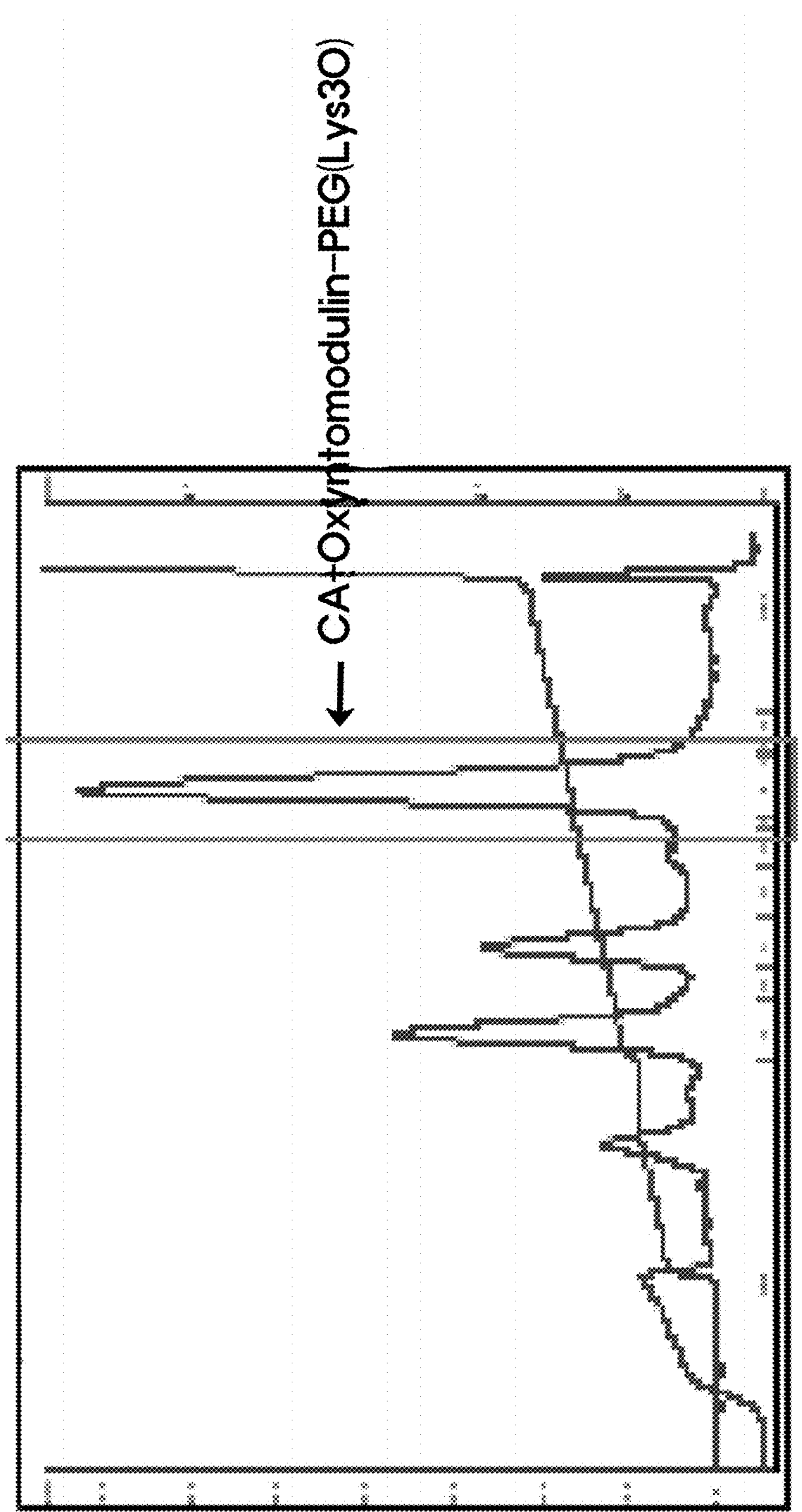
FIG. 12: a purification profile of positional isomers of imidazo-acetyl oxyntomodulin-PEG using SOURCE S column.
Figure 13:
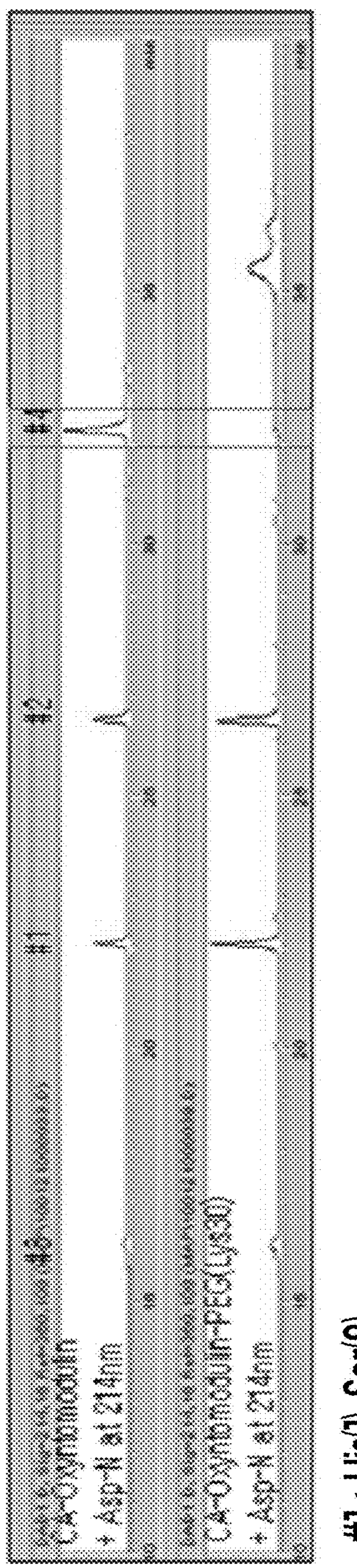
FIG. 13: an analysis profile of Lys30-pegylated isomers of oxyntomodulin by peptide mapping.

Isomers purified using SOURCE Q column was shown in FIG. 12, and the peptide mapping using an Asp-N protease was shown in FIG. 13. As shown FIG. 13, a part of #4:Asp (22)-(37) disappeared by PEG-modification at Lys30.

Example 13

Preparation of a Conjugate of Imidazo-Acetyl Oxyntomodulin (Lys30)-PEG and Immunoglobulin Fc The imidazo-acetyl oxyntomodulin-PEG (Lys30) conjugate and an immunoglobulin Fc (Hanmi Pharm. Co. Ltd., Korea) were subjected to a reaction at 4° C. for 16 hours at a molar ratio of 1:10, with a total protein concentration of 20 mg/mL. At this time, 100 mM potassium phosphate (pH 6.0) was used as a reaction medium, and 20 mM $NaCNBH_3$ as a reducing agent was added thereto. After the reaction was terminated, the reaction mixture was purified by using SOURCE 15Q column, under the following condition.

Column: SOURCE Q

Flow rate: 2.0 mL/min

Figure 14:
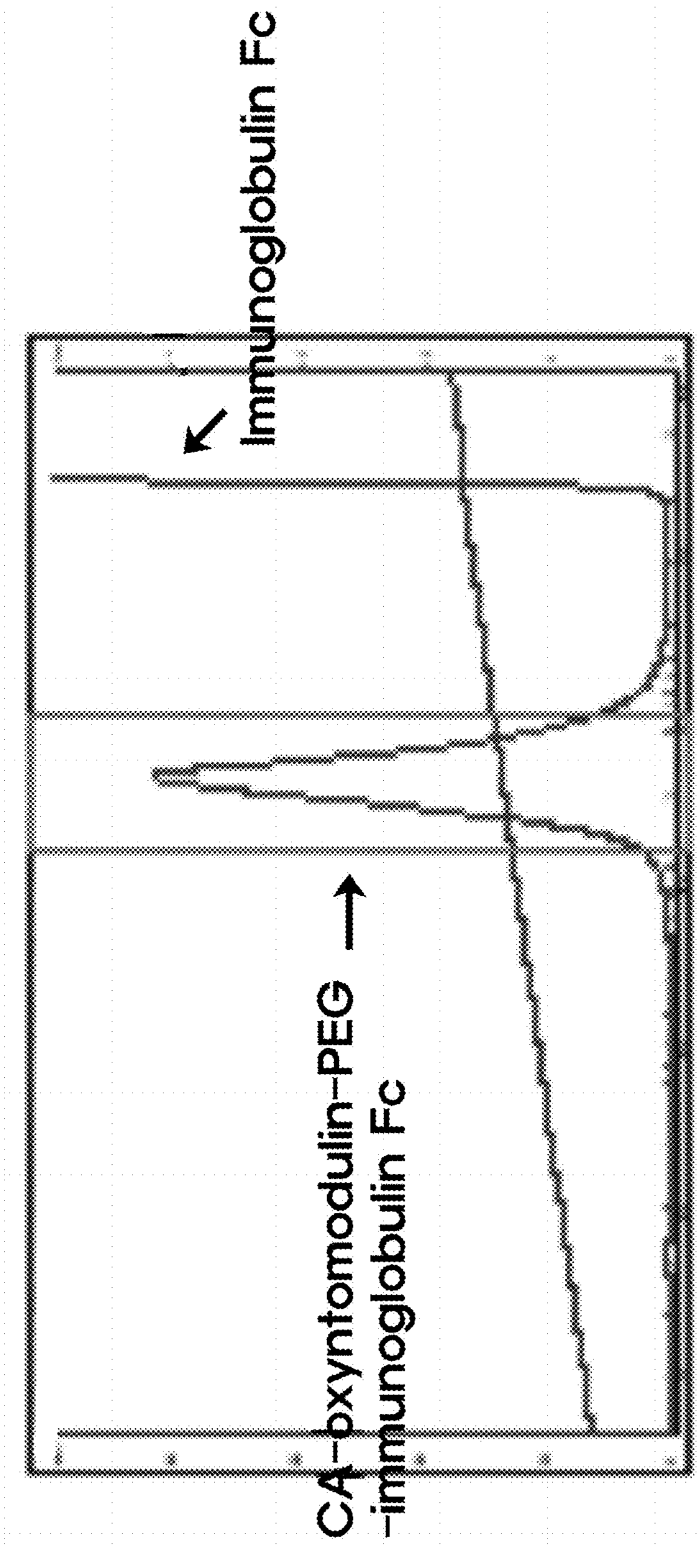
FIG. 14: a purification profile of a conjugate of imidazo-acetyl oxyntomodulin-PEG and immunoglobulin Fc using SOURCE Q column.
Figure 15:
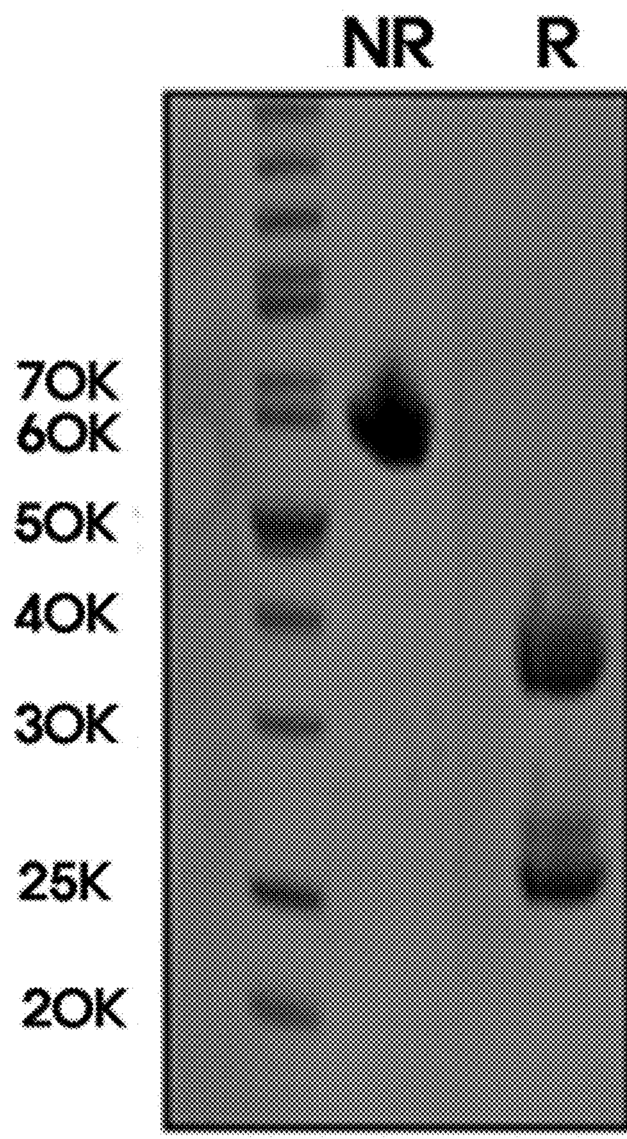
FIG. 15: an SDS-PAGE analysis of a conjugate of imidazo-acetyl oxyntomodulin-PEG and immunoglobulin Fc.

Eluting solution: A (20 mM Tris-HCl, pH 7.5) and B (A+1M NaCl); Gradient A 0→20%, 100 min The chromatogram which is achieved by linking a Lys30-pegylated CA-oxyntomodulin with an immunoglobulin Fc and purifying the conjugate using SOURCE Q was shown in FIG. 14, and SDS-PAGE results of a conjugate of CA-oxyntomodulin (Lys30)-PEG and immunoglobulin Fc were shown in FIG. 15. As shown in FIG. 15, a single band with 60K was observed under a non-reducing condition, and two bands with 35K and 25K were observed under a reducing condition.

Example 14

Preparation and isolation of pegylated oxyntomodulin analogue (Lys27) conjugate <14-1> Preparation of pegylated oxyntomodulin analogue (Lys27) conjugate To pegylate 3.4K PropionALD(2) PEG to a lysine of an oxnytomodulin analogue ([20Asp, 24Ala, 27Lys, 28Ser]-oxyntomodulin-[Deletion30-37]), the PEG and the oxyntomodulin analogue (Anygen, Korea) were subjected to a reaction at 4° C. for 3.5 hours at a molar ratio of 1:15, with a peptide concentration of 3 mg/mL. At this time, 100 mM Na-Borate buffer (pH 9.0) containing 45% isopropanol was used as a reaction medium, and 20 mM NaCNBH3 as a reducing agent was added thereto.

<14-2> Isolation of Positional Isomer

Figure 16:
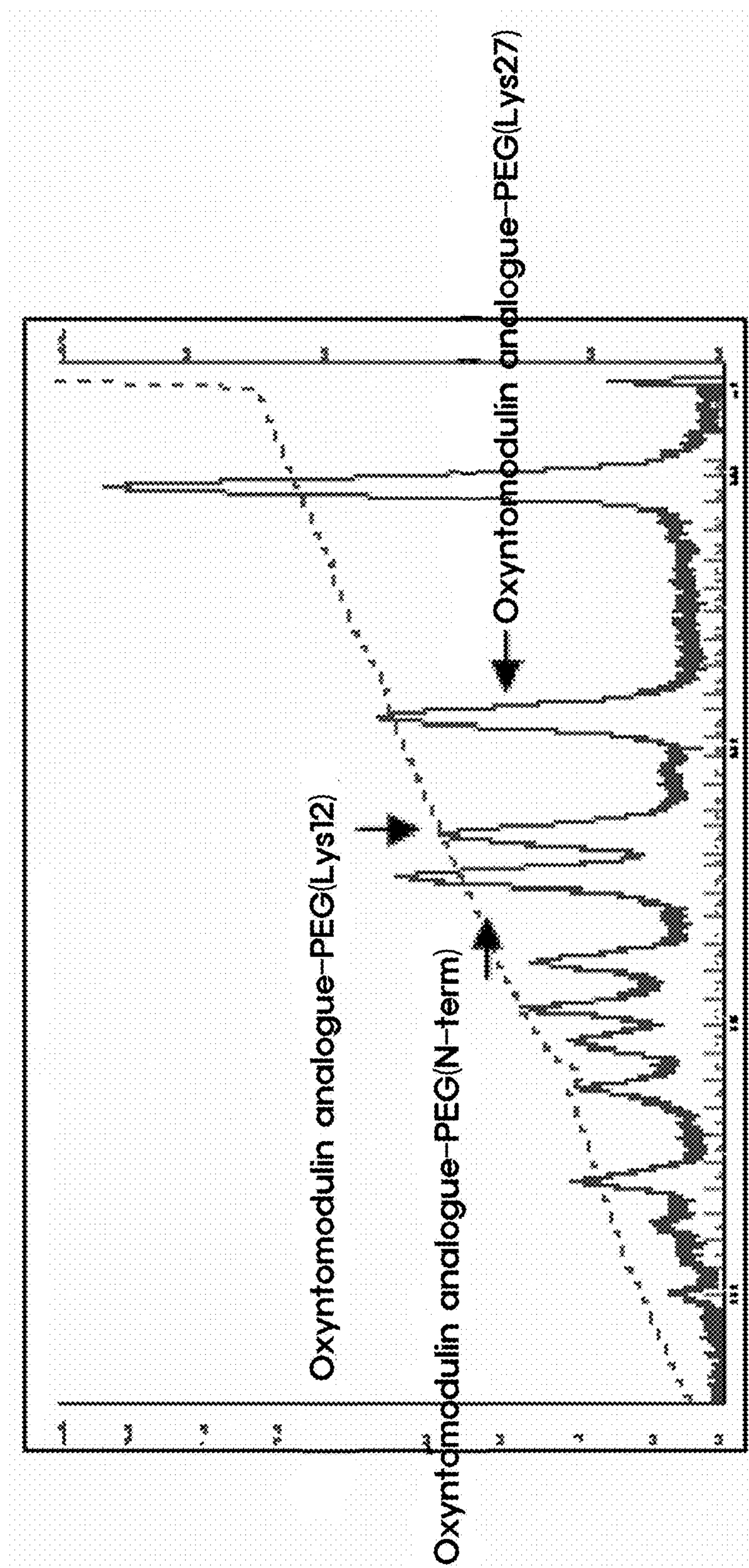
FIG. 16: a purification profile of positional isomers of oxyntomodulin analogue-PEG using SOURCE S column.
Figure 17:
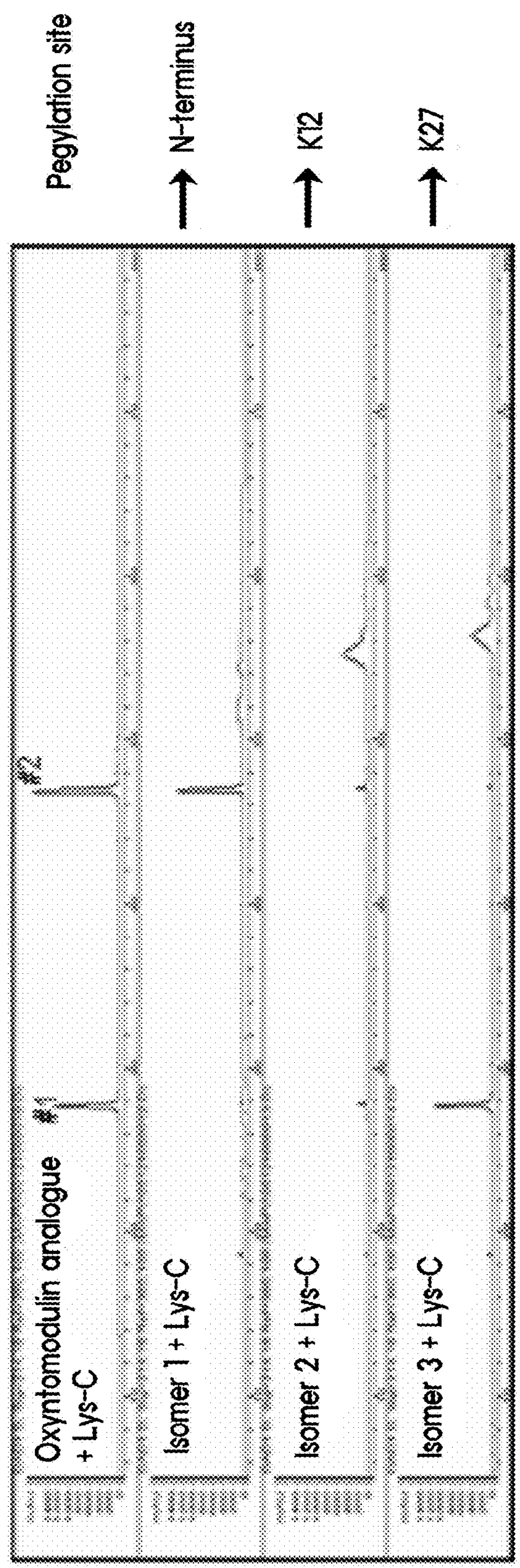
FIG. 17: an analysis profile of Lys27-pegylated isomers of oxyntomodulin analogue by peptide mapping.

Lys27-pegylated positional isomers were purified from the reaction mixture by using SOURCE 15S column (XK 16 mL, Amersham Bioscience). The conditions of purification and isolation were same with those described in Example 11. In this process, ethanol was used in the purification solution to facilitate the isolation of isomers (FIG. 16). The lysine selectivities of the purified mono-pegylated oxyntomodulin analogues were confirmed by peptide mapping method using Lys-C protease (FIG. 17). As shown in FIG. 17, a #2 part disappeared by PEG-modification at Lys27.

Example 15

Preparation and isolation of pegylated imidazo-acetyl oxyntomodulin analogue (Lys27) conjugate <15-1> Preparation of pegylated imidazo-acetyl oxyntomodulin analogue (Lys27) conjugate To pegylate 3.4K PropionALD(2) PEG to the Lys27 of an imidazo-acetyl oxyntomodulin analogue ([20Asp, 24Ala, 27Lys, 28Ser])-oxyntomodulin-[Deletion30-37]), the imidazo-acetyl oxyntomodulin analogue (Anygen, Korea) and the PEG were subjected to a reaction at 4° C. for 2.5 hours at a molar ratio of 1:10, with a total protein concentration of 3 mg/mL. At this time, 100 mM HEPES (pH 7.5) containing 45% isopropanol was used as a reaction medium, and 20 mM $NaCNBH_3$ as a reducing agent was added thereto.

<15-2> Isolation of Positional Isomer

Figure 18:
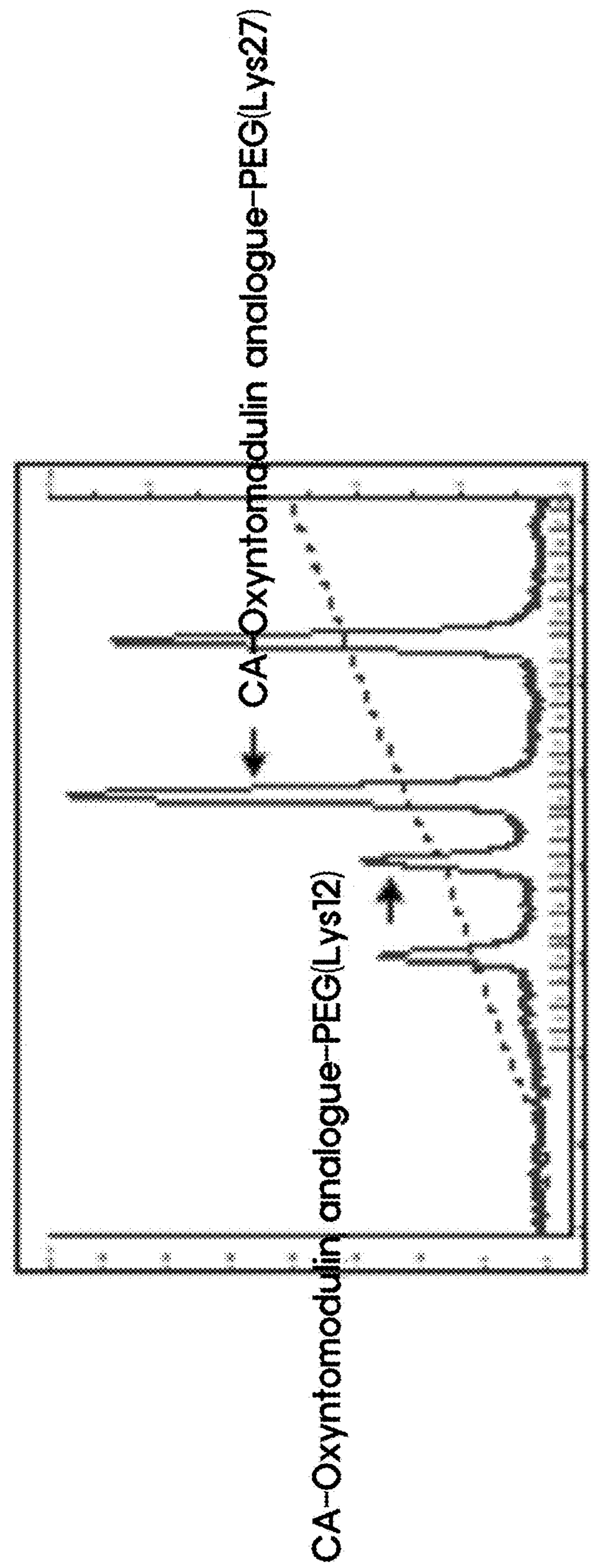
FIG. 18: a purification profile of positional isomers of imidazo-acetyl oxyntomodulin analogue-PEG using SOURCE S column.
Figure 19:
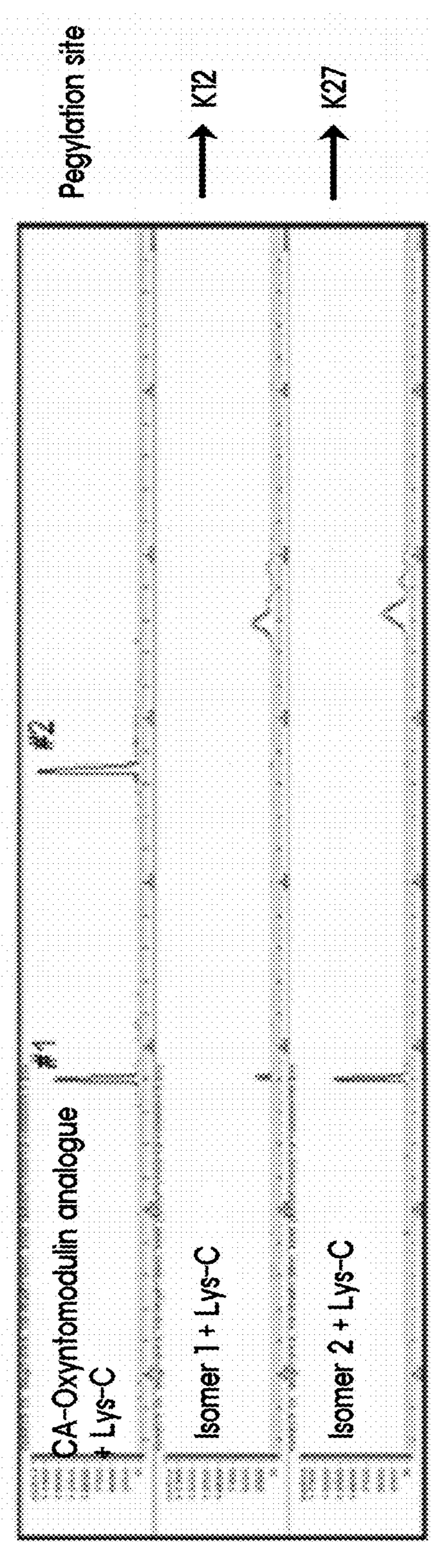
FIG. 19: an analysis profile of Lys27-pegylated isomers of imidazo-acetyl oxyntomodulin analogue by peptide mapping.

Lys27-pegylated positional isomers were purified from the reaction mixture by using SOURCE 15S column (XK 16 mL, Amersham Bioscience). The conditions of purification and isolation were same with those described in Example 11. In this process, ethanol was used in the purification solution to facilitate the isolation of isomers (FIG. 18). The lysine selectivities of the purified mono-pegylated oxyntomodulin analogues were confirmed by peptide mapping method using Lys-C protease (FIG. 19). As shown in FIG. 19, a #2 part disappeared by PEG-modification at Lys27.

Example 16

Preparation and Isolation of a Conjugate of Pegylated Imidazo-Acetyl Oxyntomodulin Analogue (Lys27) and Immunoglobulin Fc The Lys27-pegylated imidazo-acetyl oxyntomodulin analogue-PEG prepared in Example 15 and an immunoglobulin Fc were subjected to a reaction at 4° C. for 16 hours at a molar ratio of 1:10, with a peptide concentration of 20 mg/mL. At this time, 100 mM potassium phosphate (pH 6.0) as a reaction medium, and 20 mM $NaCNBH_3$ as a reducing agent was added thereto. After the reaction was terminated, the reaction mixture was purified by using SOURCE 15Q column, under the following condition.

Column: SOURCE Q

Flow rate: 2.0 mL/min

Figure 20:
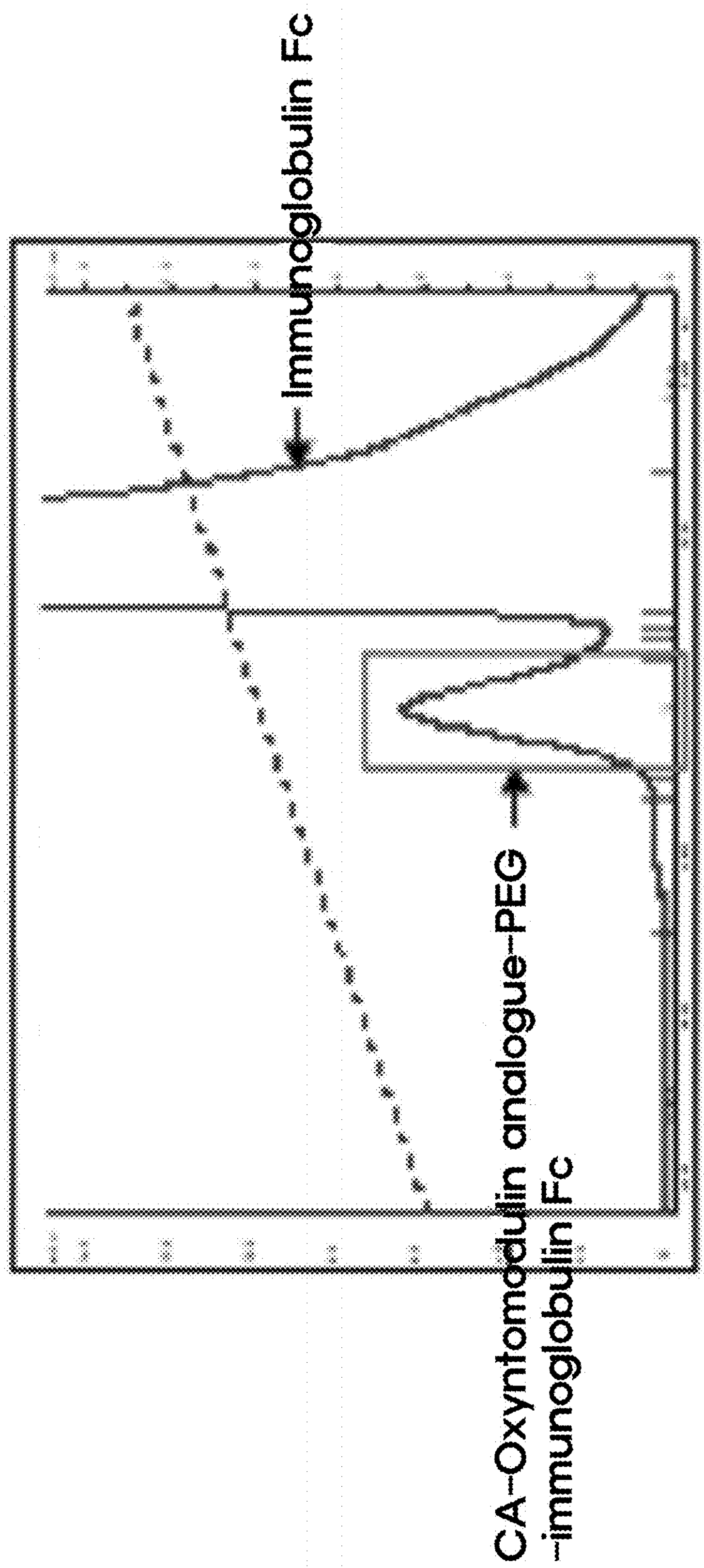
FIG. 20: a purification profile of a conjugate of imidazo-acetyl oxyntomodulin analog-PEG and immunoglobulin Fc using SOURCE Q column.
Figure 21:
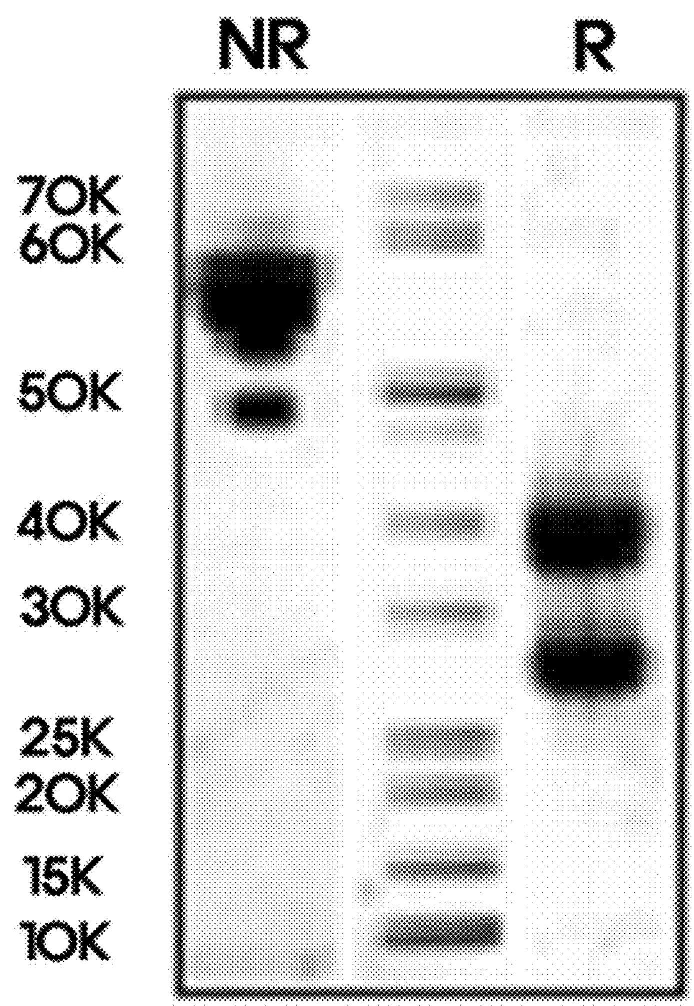
FIG. 21: an SDS-PAGE analysis of a conjugate of imidazo-acetyl oxyntomodulin analog-PEG and immunoglobulin Fc.

Eluting solution: A (20 mM Tris-HCl, pH 7.5) and B (A+1M NaCl); Gradient A 0→20%, 100 min The chromatogram which is achieved by linking a Lys27-pegylated CA-oxyntomodulin analogue with an immunoglobulin Fc and purifying the conjugate using SOURCE Q was shown in FIG. 20, and SDS-PAGE results of a conjugate of CA-oxyntomodulin analogue (Lys27)-PEG and immunoglobulin Fc were shown in FIG. 21. As shown in FIG. 21, a single band with 60K was observed under a non-reducing condition, and two bands with 35K and 25K were observed under a reducing condition.

Example 17

Preparation and Isolation of Pegylated GLP-1 (Lys34) Conjugate

<17-1> Preparation of Pegylated GLP-1 (Lys34) Conjugate

To pegylate 3.4K PropionALD(2) PEG to the Lysine residue of a GLP-1, the GLP-1 and the PEG were subjected to a reaction at 4° C. for 3.5 hours at a molar ratio of 1:15, with a total protein concentration of 3 mg/mL. At this time, 100 mM Na-Borate (pH 9.0) containing 45% isopropanol was used as a reaction medium, and 20 mM $NaCNBH_3$ as a reducing agent was added thereto.

<17-2> Isolation of Positional Isomer

Figure 22:
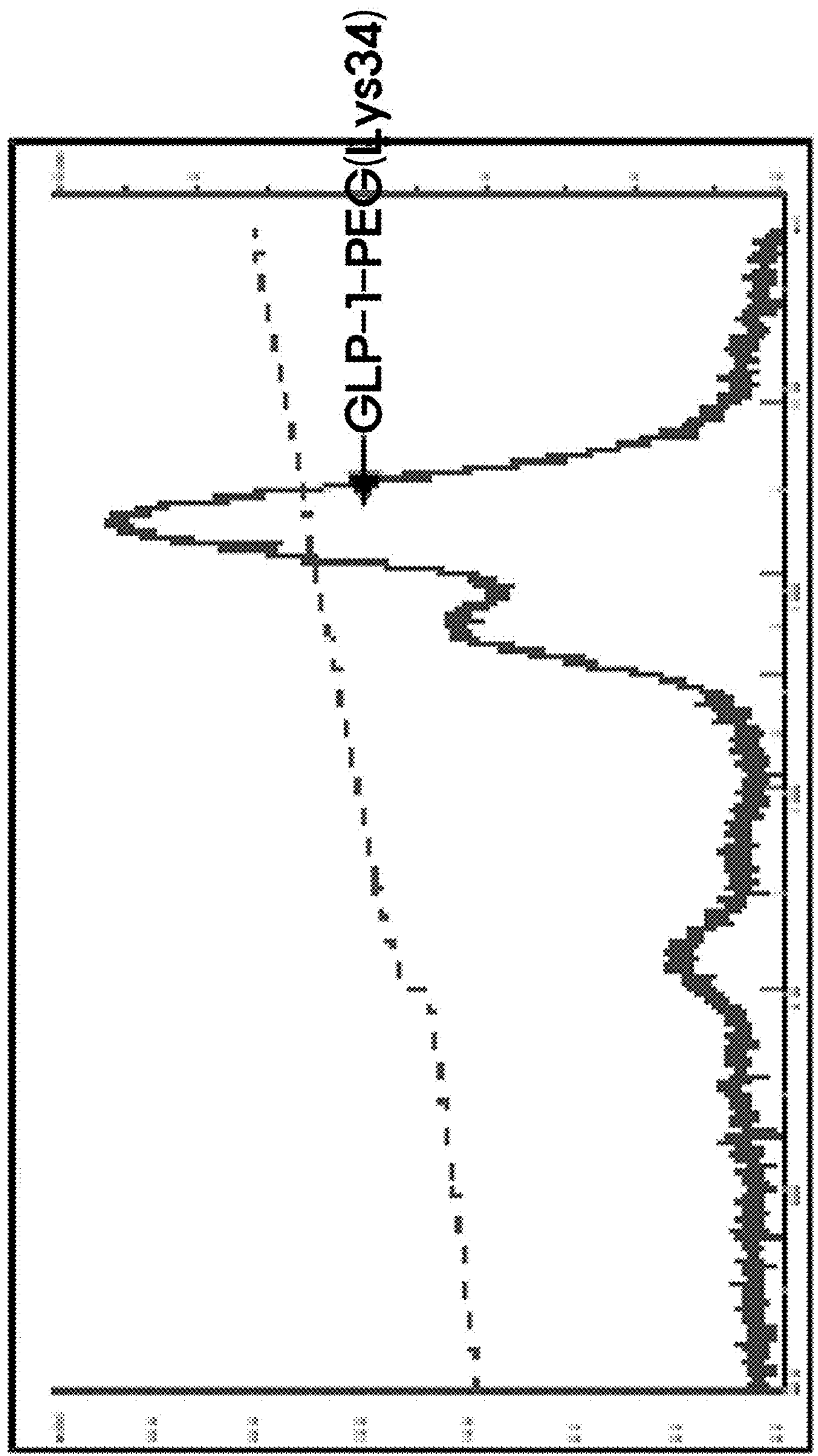
FIG. 22: a purification profile of positional isomers of GLP-1-PEG using SOURCE S column.
Figure 23:
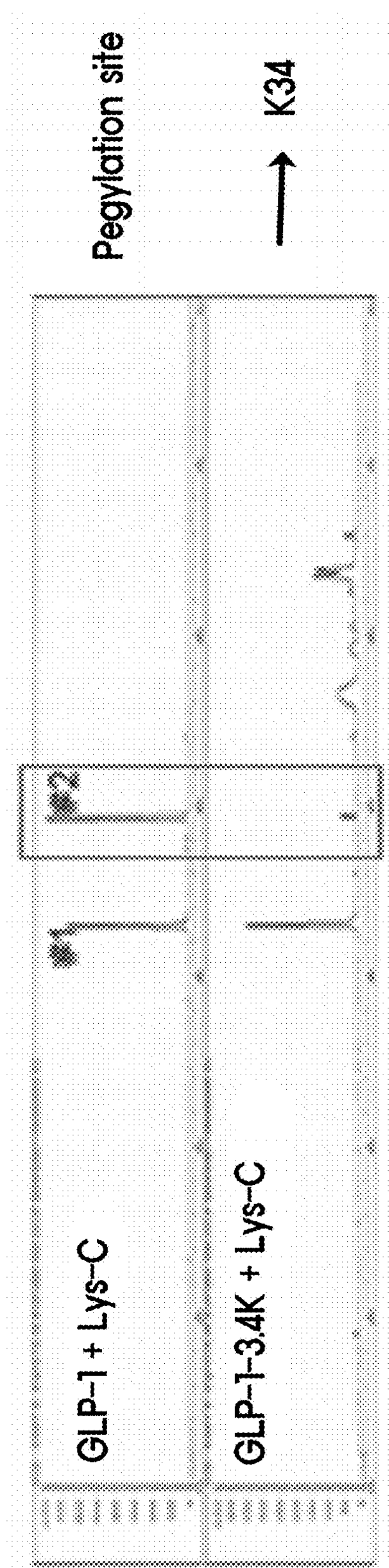
FIG. 23: an analysis profile of Lys34-pegylated isomers of GLP-1 by peptide mapping.

Lys34-pegylated positional isomers were purified from the reaction mixture by using SOURCE 15S column (XK 16 mL, Amersham Bioscience). In this process, ethanol was used in the purification solution to facilitate the isolation of isomers (FIG. 22). The lysine selectivities of the purified mono-pegylated oxyntomodulin analogues were confirmed by peptide mapping method using Lys-C protease (FIG. 23).

Column: SOURCE S

Flow rate: 2.0 mL/min

Eluting solution: A (20 mM Na-citrate, pH 3.0+45% ethanol) and B (A+1M KCl); Gradient A 0→3%, 1 min, Gradient B 3→40%, 150 min As shown in FIG. 23, a #2 part disappeared by PEG-modification at Lys34.

Example 18

Preparation and Isolation of Pegylated Imidazo-Acetyl GLP-1 (Lys34) Conjugate <18-1> Preparation of Pegylated Imidazo-Acetyl GLP-1 (Lys34) Conjugate To pegylate 3.4K PropionALD(2) PEG to the Lysine residue of an imidazo-acetyl GLP-1, the imidazo-acetyl GLP-1 and the PEG were subjected to a reaction at 4° C. for 4 hours at a molar ratio of 1:10, with a total protein concentration of 3 mg/mL. At this time, 100 mM HEPES (pH 7.5) containing 45% isopropanol was used as a reaction medium, and 20 mM $NaCNBH_3$ as a reducing agent was added thereto.

<18-2> Isolation of Positional Isomer

Figure 24:
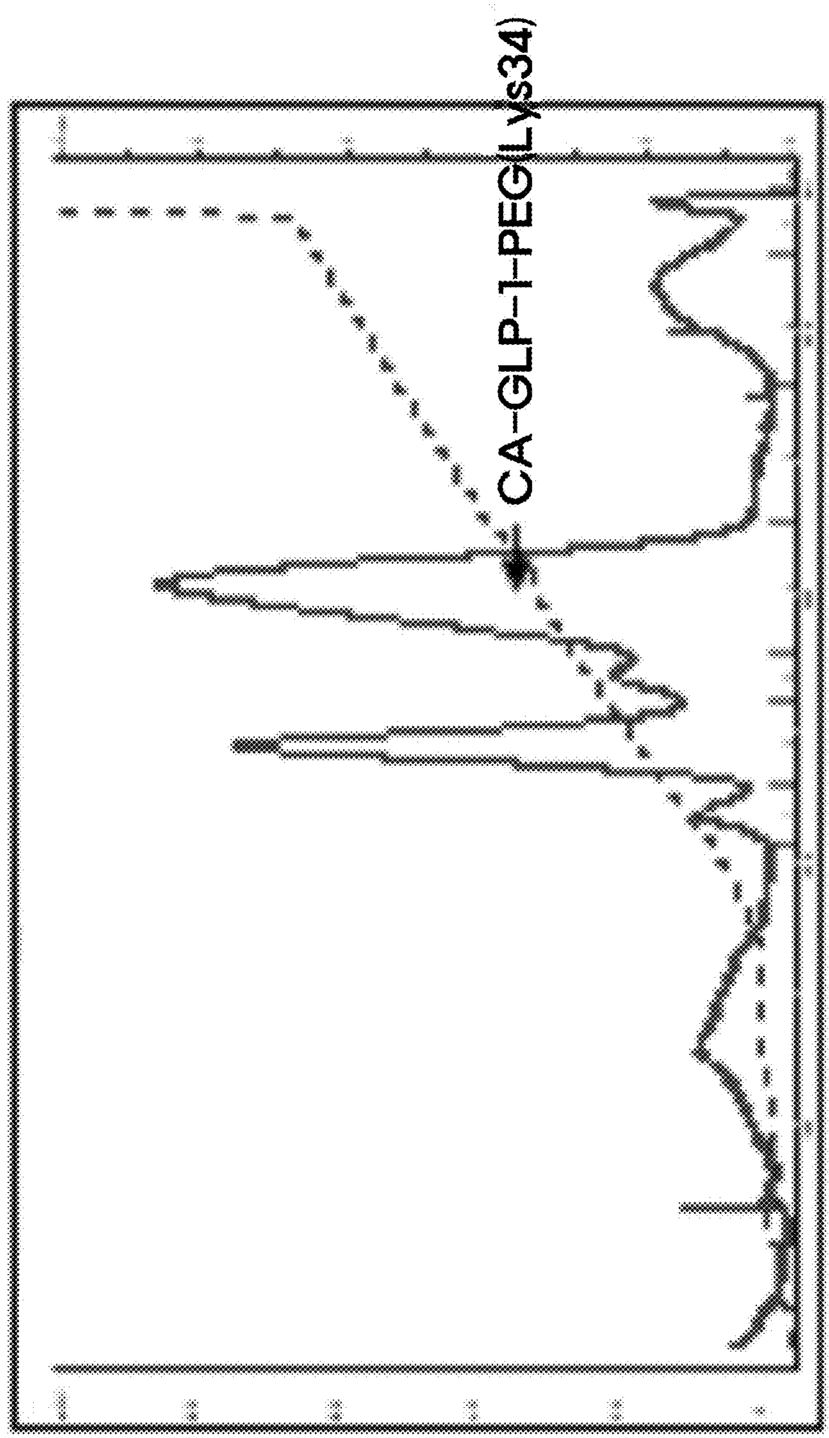
FIG. 24: a purification profile of positional isomers of imidazo-acetyl GLP-1-PEG using SOURCE S column.
Figure 25:
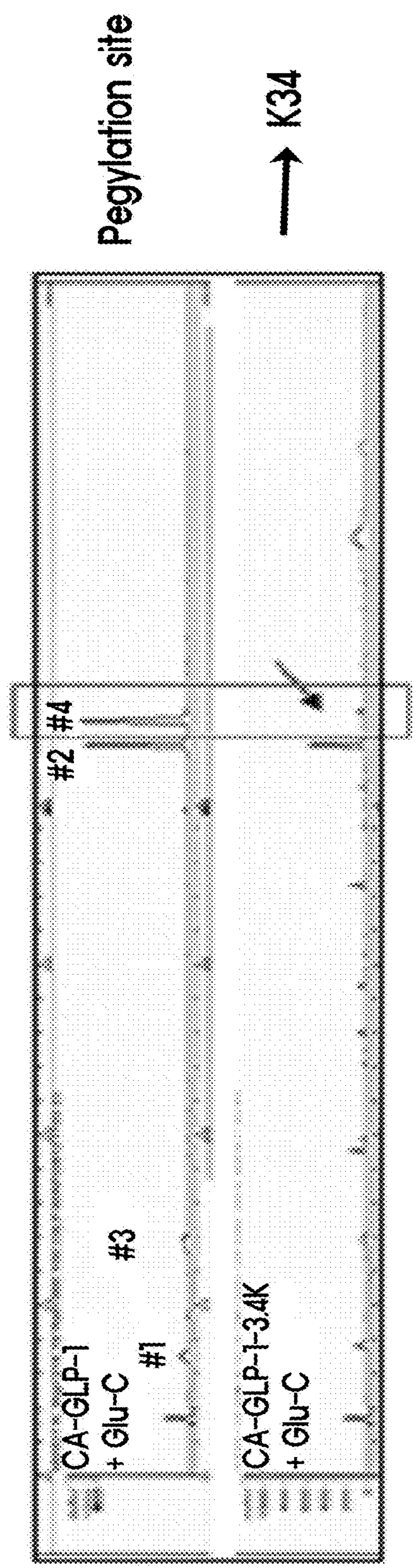
FIG. 25: an analysis profile of Lys34-pegylated isomers of imidazo-acetyl GLP-1 by peptide mapping.

Lys34-pegylated positional isomers were purified from the reaction mixture by using SOURCE 15S column (XK 16 mL, Amersham Bioscience). In this process, ethanol was used in the purification solution to facilitate the isolation of isomers (FIG. 24). The lysine selectivities of the purified mono-pegylated oxyntomodulin analogues were confirmed by peptide mapping method using Glu-C protease (FIG. 25).

Column: SOURCE S

Flow rate: 2.0 mL/min

Eluting solution: A (20 mM Na-citrate, pH 3.0+45% ethanol) and B (A+1M KCl); Gradient A 0→3%, 1 min, Gradient B 3→40%, 150 min As shown in FIG. 25, a #4 part disappeared by PEG-modification at Lys34.

Example 19

Preparation and Isolation of a Conjugate of Pegylated Imidazo-Acetyl GLP-1 (Lys34) and Immunoglobulin Fc The Lys34-pegylated imidazo-acetyl GLP-1-PEG prepared in Example 18 and an immunoglobulin Fc were subjected to a reaction at 4° C. for 17 hours at a molar ratio of 1:8, with a peptide concentration of 50 mg/mL. At this time, 100 mM potassium phosphate (pH 6.0) as a reaction medium, and 20 mM $NaCNBH_3$ as a reducing agent was added thereto. After the reaction was terminated, the reaction mixture was purified by using SOURCE Phe column, under the following condition.

Column: SOURCE Phe

Flow rate: 2.0 mL/min

Figure 26:
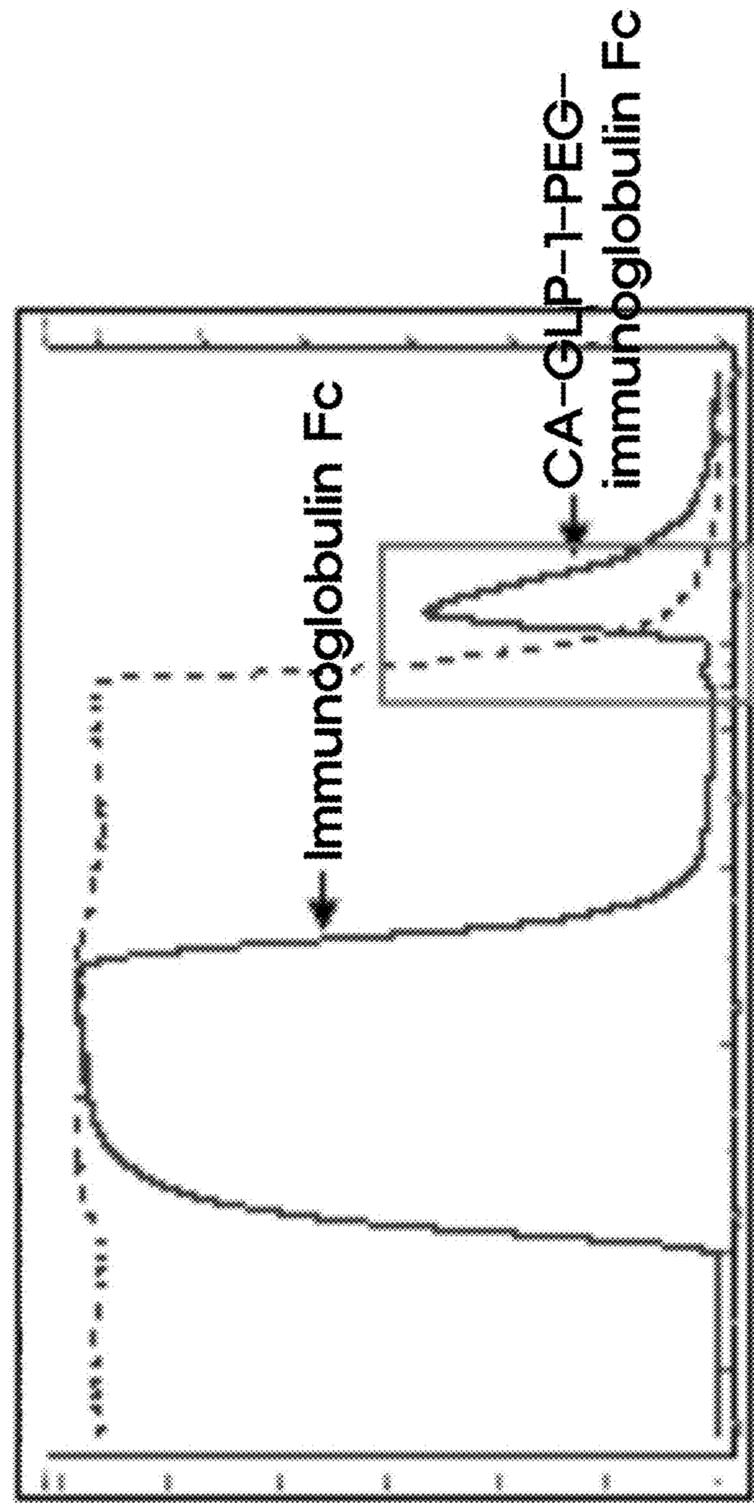
FIG. 26: a purification profile of a conjugate of imidazo-acetyl GLP-1-PEG and immunoglobulin Fc using SOURCE Phe column.
Figure 27:
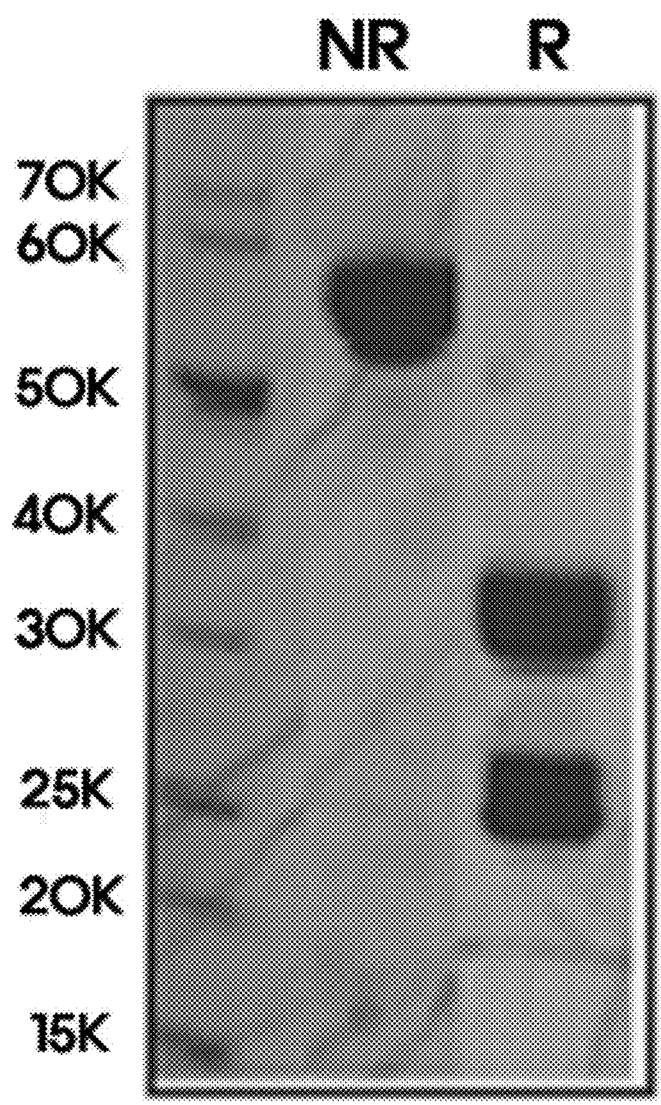
FIG. 27: an SDS-PAGE analysis of a conjugate of imidazo-acetyl GLP-1-PEG and immunoglobulin Fc.

Eluting solution: A (20 mM Tris-HCl, pH 7.5) and B (A+2M NaCl); Gradient A 100→0%, 100 min The chromatogram which is achieved by linking a Lys34-pegylated CA-GLP-1 isomer with an immunoglobulin Fc and purifying the conjugate using SOURCE Phe was shown in FIG. 26, and SDS-PAGE results of a conjugate of CA-GLP-1 (Lys34)-PEG and immunoglobulin Fc were shown in FIG. 27. As shown in FIG. 27, a single band with 60K was observed under a non-reducing condition, and two bands with 35K and 25K were observed under a reducing condition.

Example 20

Preparation and Isolation of Pegylated GLP-2 (Lys30) Conjugate

<20-1> Preparation of Pegylated GLP-2 (Lys30) Conjugate

To pegylate 3.4K PropionALD(2) PEG to the Lysine residue of a GLP-2 (Anygen, Korea), the GLP-2 and the PEG were subjected to a reaction at 4° C. for 3 hours at a molar ratio of 1:12, with a total protein concentration of 5 mg/mL. At this time, 100 mM Na-Borate (pH 9.0) containing 45% isopropanol was used as a reaction medium, and 20 mM $NaCNBH_3$ as a reducing agent was added thereto.

<20-2> Isolation of Positional Isomer

Figure 28:
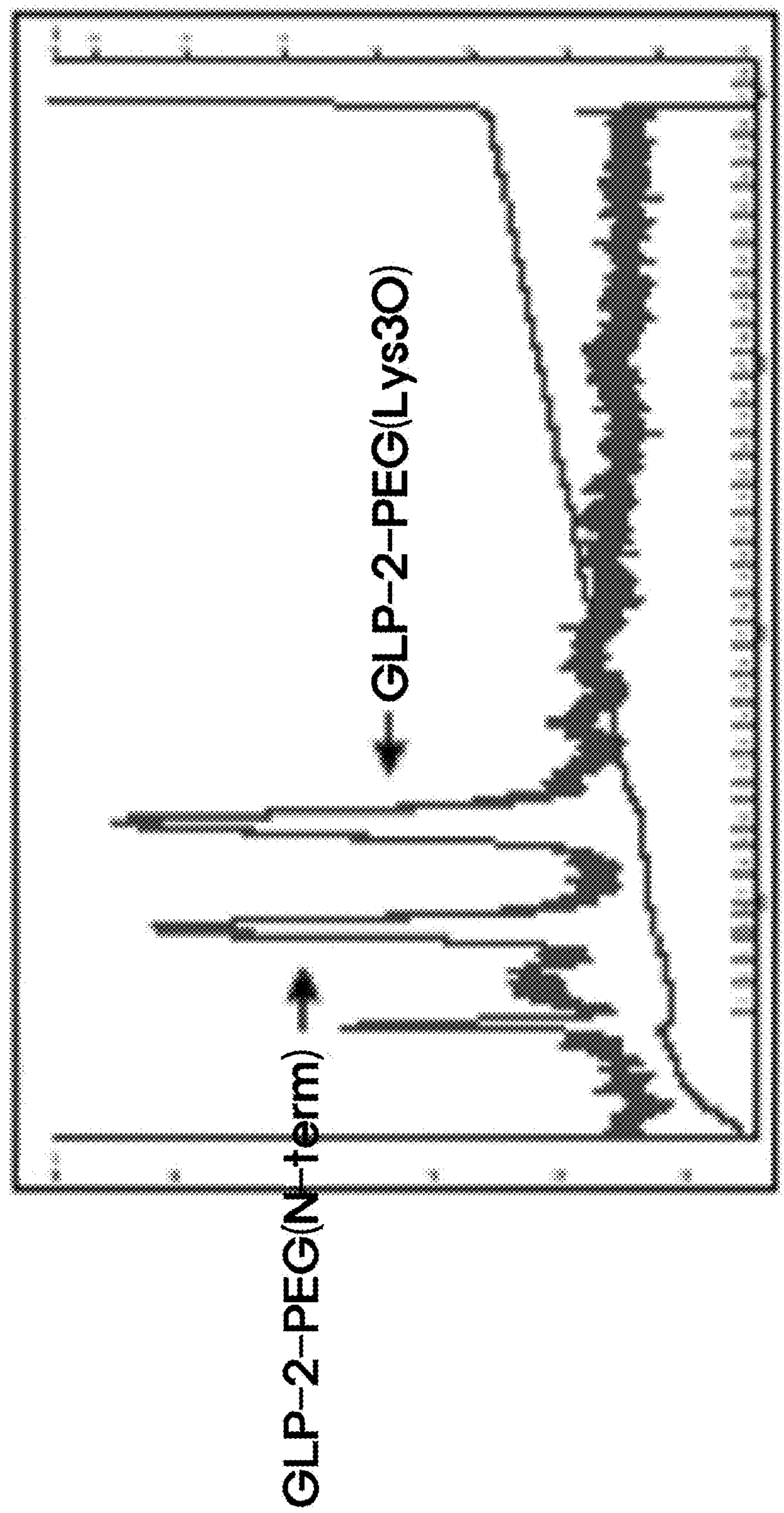
FIG. 28: a purification profile of positional isomers of GLP-2-PEG using SOURCE S column.
Figure 29:
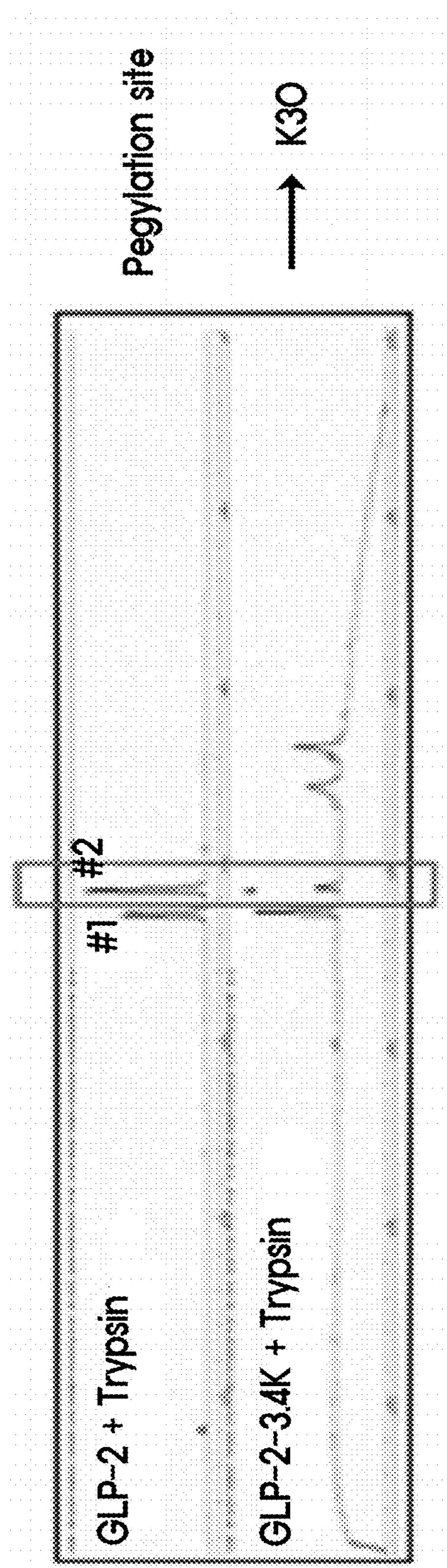
FIG. 29: an analysis profile of Lys30-pegylated isomers of GLP-2 by peptide mapping.

Lys30-pegylated positional isomers were purified from the reaction mixture by using SOURCE 15S column (XK 16 mL, Amersham Bioscience). In this process, ethanol was used in the purification solution to facilitate the isolation of isomers (FIG. 28). The lysine selectivities were confirmed by peptide mapping method using a trypsin protease (FIG. 29).

Column: SOURCE S

Flow rate: 2.0 mL/min

Eluting solution: A (20 mM Na-citrate, pH 3.0+45% ethanol) and B (A+1M KCl); Gradient A 0→3%, 1 min, Gradient B 3→40%, 150 min As shown in FIG. 29, a #2 part disappeared by PEG-modification at Lys30.

Example 21

Preparation and Isolation of Pegylated Imidazo-Acetyl GLP-2 (Lys30) Conjugate

<21-1> Preparation of Pegylated Imidazo-Acetyl GLP-2 (Lys30) Conjugate

To pegylate 3.4K PropionALD(2) PEG to the Lysine30 residue of an imidazo-acetyl GLP-2 (Anygen, Korea), the imidazo-acetyl GLP-2 and the PEG were subjected to a reaction at 4° C. for 6 hours at a molar ratio of 1:20, with a total protein concentration of 3 mg/mL. At this time, 100 mM HEPES (pH 7.5) containing 45% isopropanol was used as a reaction medium, and 20 mM $NaCNBH_3$ as a reducing agent was added thereto.

<21-2> Isolation of Positional Isomer

Figure 30:
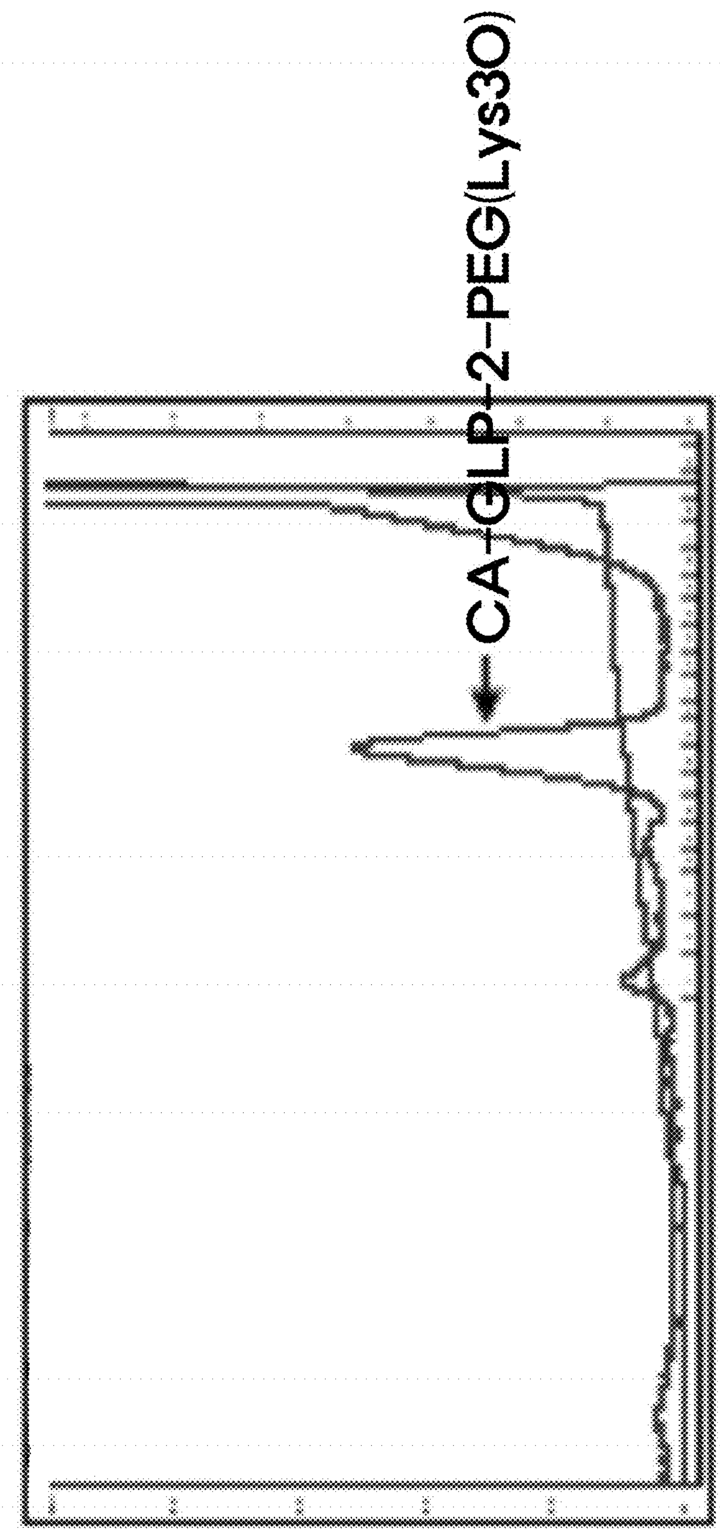
FIG. 30: a purification profile of positional isomers of imidazo-acetyl GLP-2-PEG using SOURCE S column.

Lys30-pegylated positional isomers were purified from the reaction mixture by using SOURCE 15S column (XK 16 mL, Amersham Bioscience). In this process, ethanol was used in the purification solution to facilitate the isolation of isomers (FIG. 30).

Column: SOURCE S

Flow rate: 2.0 mL/min

Eluting solution: A (20 mM Na-citrate, pH 3.0+45% ethanol) and B (A+1M KCl); Gradient A 0→3%, 1 min, Gradient B 3→40%, 150 min Example 22

Preparation and Isolation of a Conjugate of Pegylated Imidazo-Acetyl GLP-2 (Lys30) and Immunoglobulin Fc The Lys30-pegylated imidazo-acetyl GLP-2-PEG prepared in Example 21 and an immunoglobulin Fc were subjected to a reaction at 4° C. for 16 hours at a molar ratio of 1:15, with a peptide concentration of 20 mg/mL. At this time, 100 mM potassium phosphate (pH 6.0) as a reaction medium, and 20 mM $NaCNBH_3$ as a reducing agent was added thereto. After the reaction was terminated, the reaction mixture was purified by using SOURCE Phe column, under the following condition.

Column: SOURCE Phe

Flow rate: 2.0 mL/min

Figure 31:
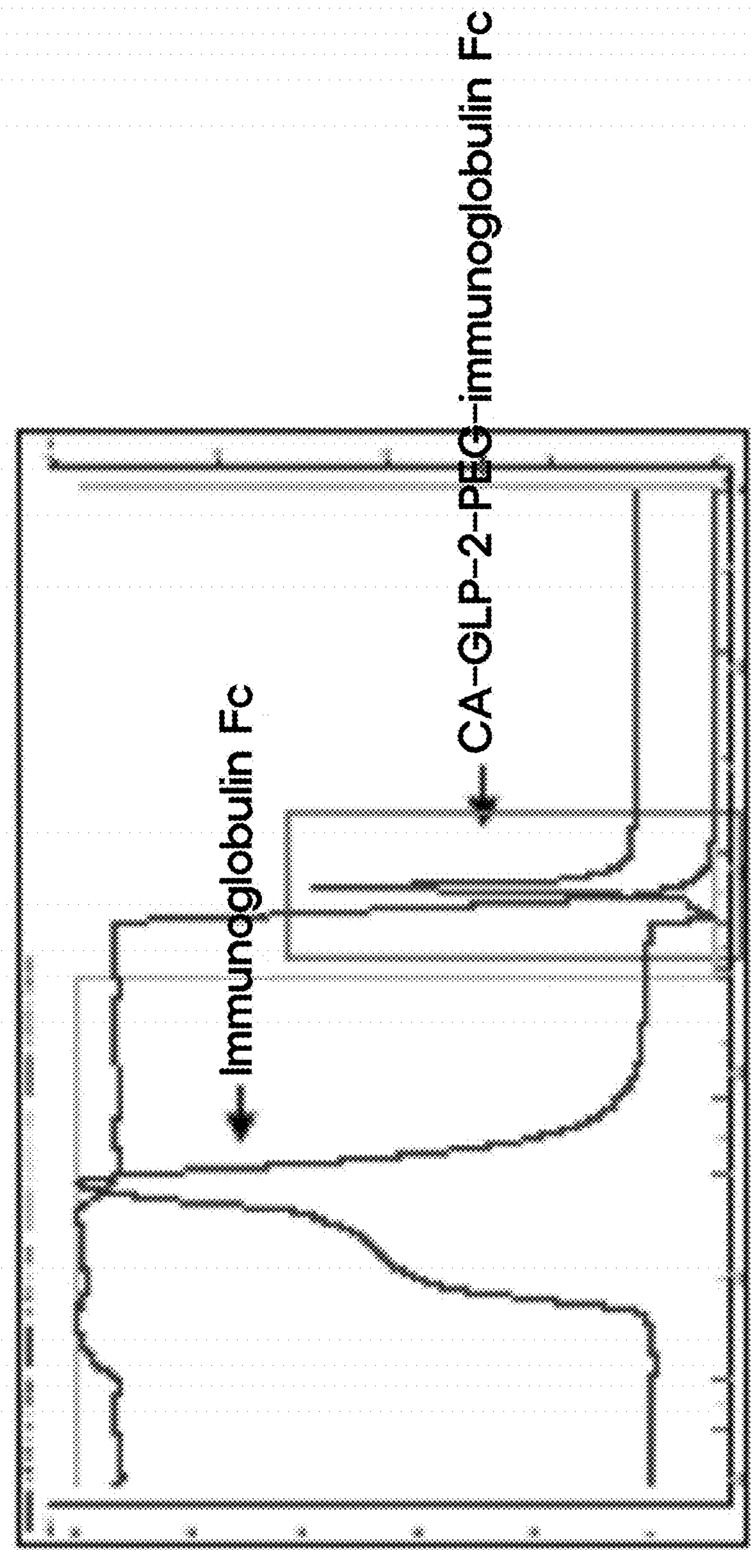
FIG. 31: a purification profile of a conjugate of imidazo-acetyl GLP-2-PEG and immunoglobulin Fc using SOURCE Phe column.
Figure 32:
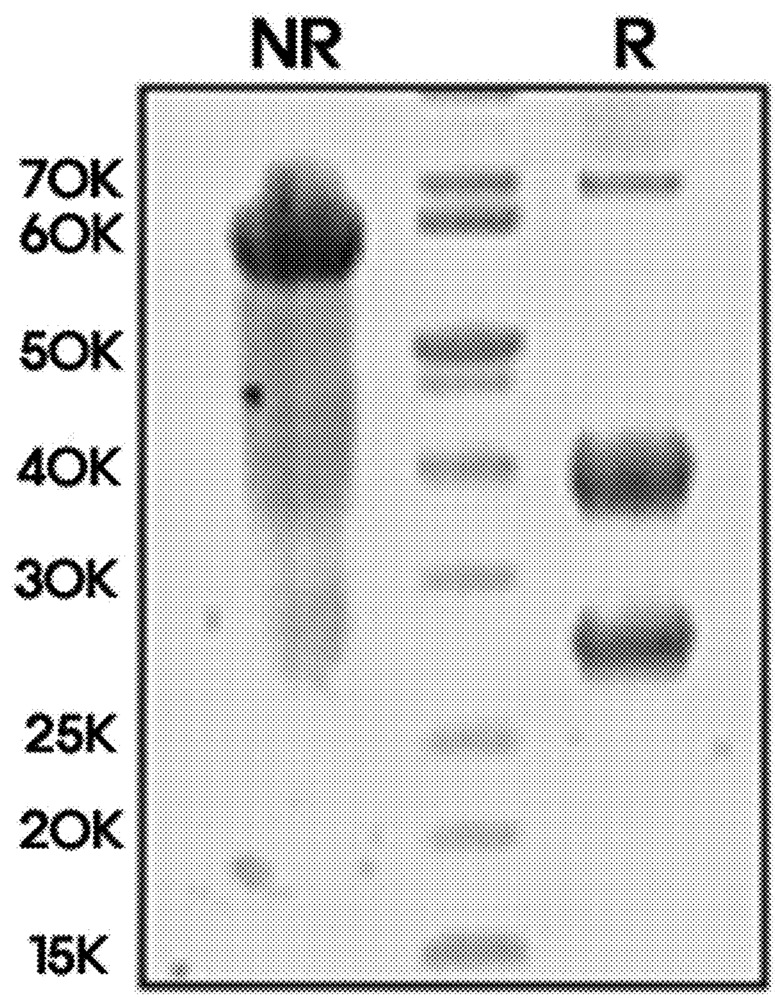
FIG. 32: an SDS-PAGE analysis of a conjugate of imidazo-acetyl GLP-2-PEG and immunoglobulin Fc.

Eluting solution: A (20 mM Tris-HCl, pH 7.5) and B (A+2M NaCl); Gradient A 100→0%, 100 min The chromatogram which is achieved by linking a Lys30-pegylated CA-GLP-2 isomer with an immunoglobulin Fc and purifying the conjugate using SOURCE Phe was shown in FIG. 31, and SDS-PAGE results of a conjugate of CA-GLP-2 (Lys30)-PEG and immunoglobulin Fc were shown in FIG. 32. As shown in FIG. 32, a single band with 60K was observed under a non-reducing condition, and two bands with 35K and 25K were observed under a reducing condition.

Example 23

Preparation and Isolation of Pegylated Human Insulin (B1Phe) Conjugate

<23-1> Preparation of Pegylated Human Insulin (B1Phe) Conjugate

To pegylate 5K PropionALD(1) methoxyPEG (PEG having one propionaldehyde group, NOF., Japan) to a N-terminal of phenylalanine which is a first amino acid of B chain in human insulin (Sigma), the PEG and the insulin hyman were subjected to a reaction at 4° C. for 12 hours at a molar ratio of 1:2, with a peptide concentration of 2.3 mg/mL. At this time, 100 mM potassium phosphate buffer (pH 6.0) was used as a reaction medium, and 20 mM $NaCNBH_3$ as a reducing agent was added thereto.

<23-2> Isolation of Positional Isomer

Figure 33:
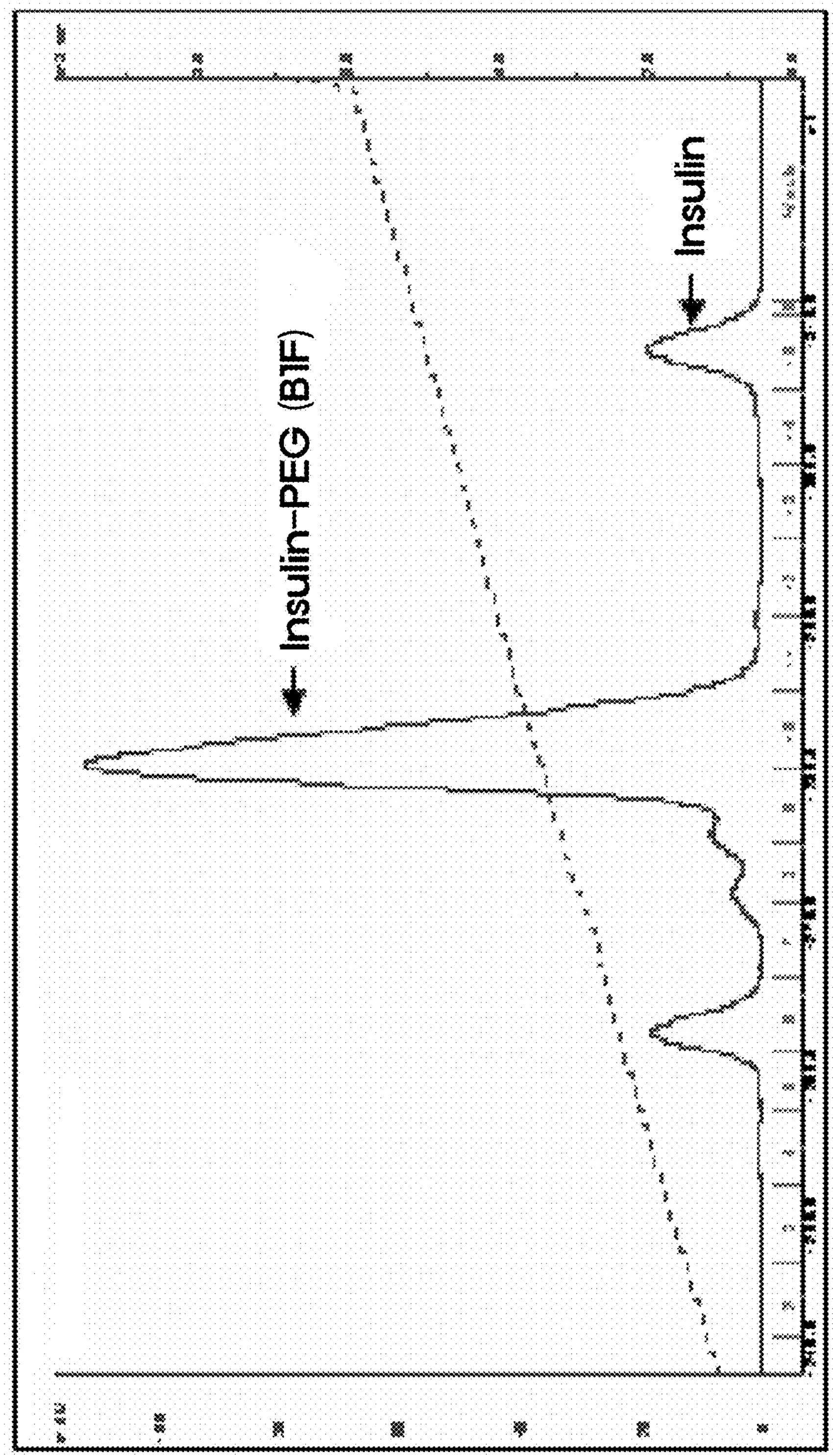
FIG. 33: a purification profile of positional isomers of human insulin-PEG (B1F) using SOURCE S column.
Figure 36:
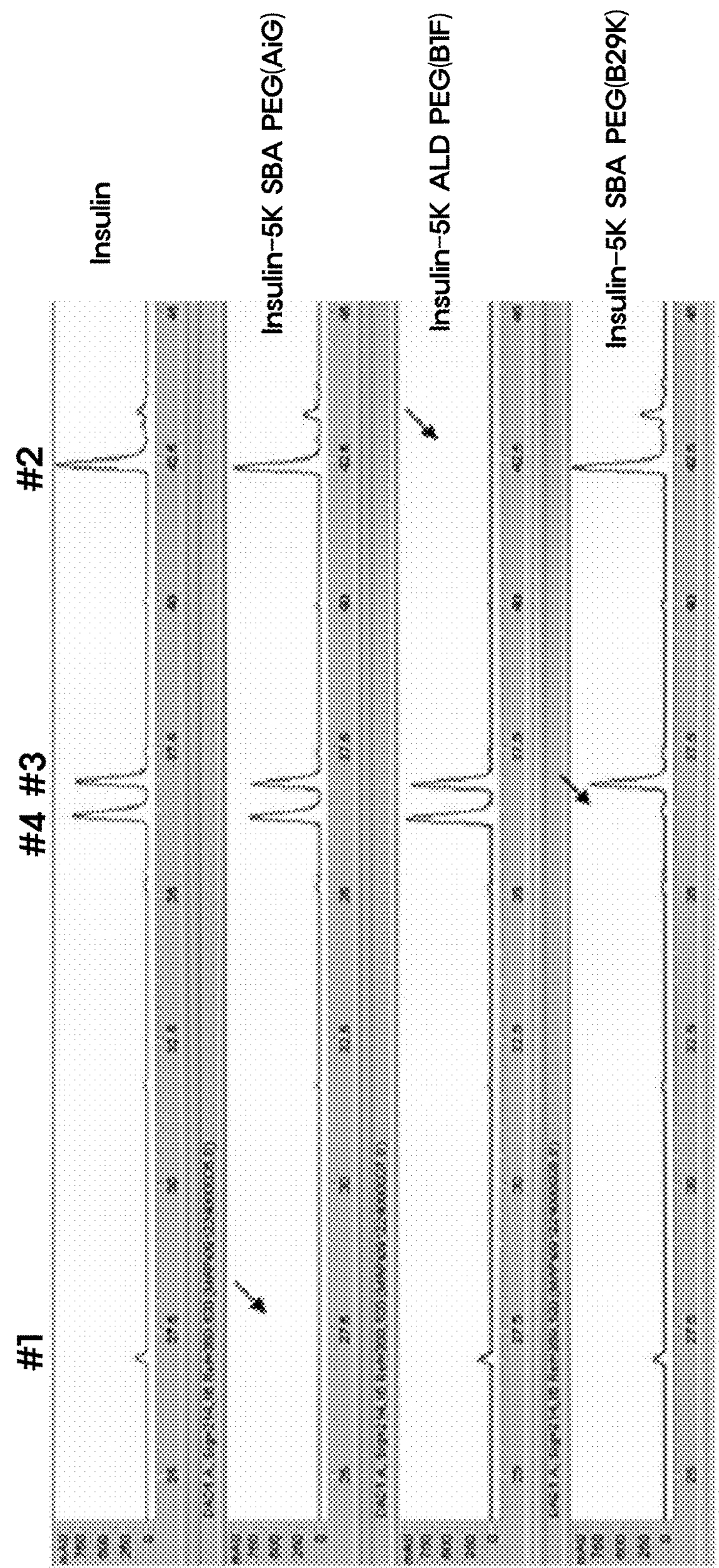
FIG. 36: an analysis profile of A1G-, B1F-, or B29K-pegylated isomers of human insulin by peptide mapping.

Positional isomers were purified from the reaction mixture by using SOURCE 15S column (XK 16 mL, Amersham Bioscience). In this process, ethanol was used in the purification solution to facilitate the isolation of isomers (FIG. 33). The mono-pegylations of eluted peaks were confirmed by SDS-PAGE analysis, and the lysine selectivities were confirmed by peptide mapping method using Glu-C protease (FIG. 36).

Column: SOURCE S

Flow rate: 2.0 mL/min

Eluting solution: A (20 mM Na-citrate, pH 2.0+60% ethanol) and B (A+0.5M KCl); Gradient A 0→3%, 1 min, Gradient B 0→50%, 80 min As shown in FIG. 36, a #2 part disappeared by PEG-modification at B1F.

Example 24

Preparation and Isolation of Pegylated Human Insulin (A1Gly) Conjugate

<24-1> Preparation of Pegylated Human Insulin (A1Gly) Conjugate

To pegylate 5K methoxyPEG-Succinimidyl Butanoate(1) (PEG having one SBA reactive group, NOF., Japan) to a N-terminal of glycine which is a first amino acid of A chain in human insulin (Sigma), the PEG and the human insulin were subjected to a reaction at 25° C. for 3 hours at a molar ratio of 1:4, with a peptide concentration of 2 mg/mL. At this time, 100 mM Na-Borate buffer (pH 9.0) containing 35% isopropanol was used as a reaction medium.

<24-2> Isolation of Positional Isomer

Figure 34:
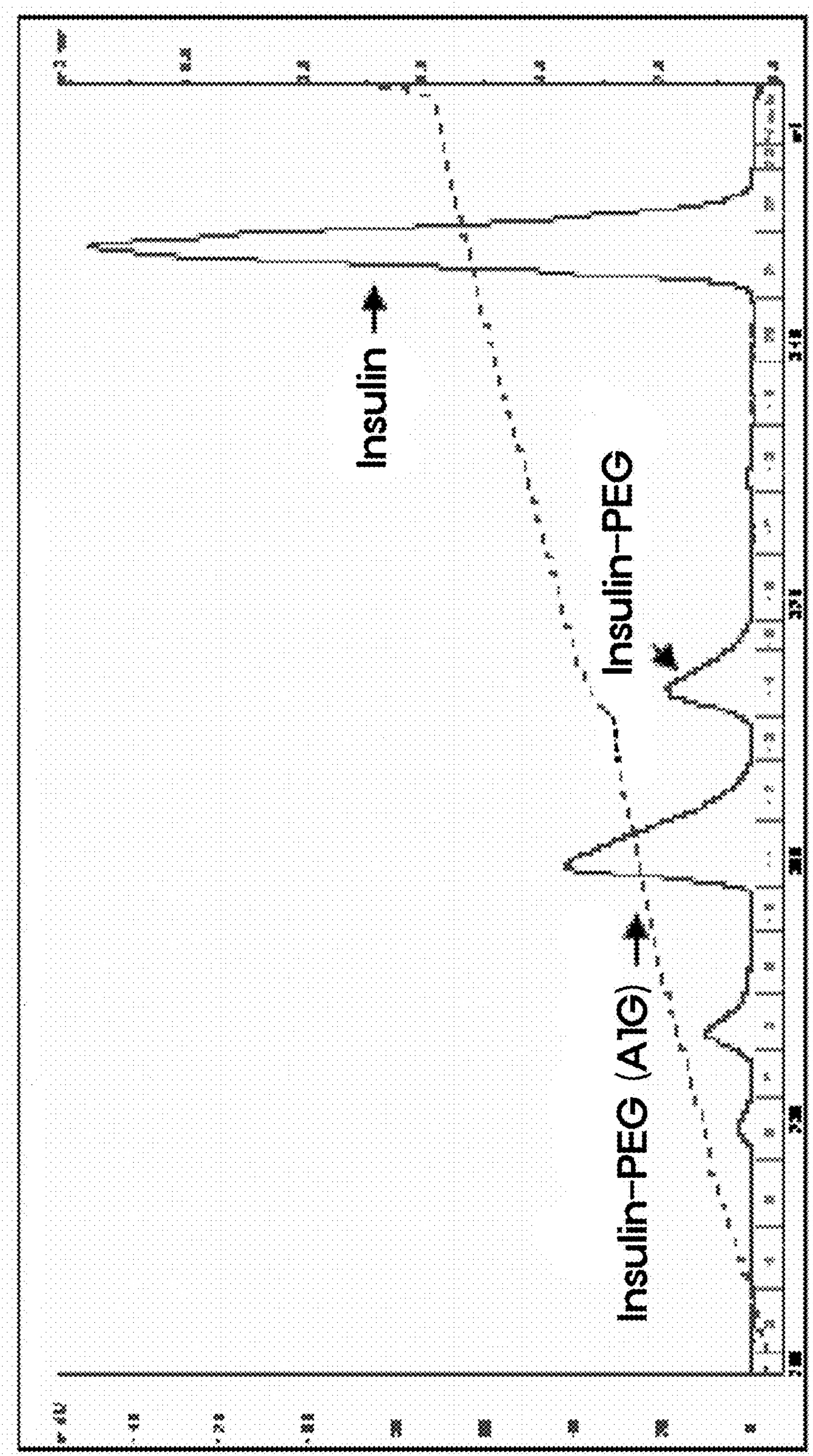
FIG. 34: a purification profile of positional isomers of human insulin-PEG (A1G) using SOURCE S column.

Positional isomers were purified from the reaction mixture by using SOURCE 15S column (XK 16 mL, Amersham Bioscience). The purification procedure was same with that described in Example 23. In this process, ethanol was used in the purification solution to facilitate the isolation of isomers (FIG. 34). The mono-pegylations of eluted peaks were confirmed by SDS-PAGE analysis, and the lysine selectivities were confirmed by peptide mapping method using Glu-C protease (FIG. 36).

As shown in FIG. 36, a #1 part disappeared by PEG-modification at A1G.

Example 25

Preparation and Isolation of Pegylated Human Insulin (B29Lys) Conjugate

<25-1> Preparation of Pegylated Human Insulin (B29Lys) Conjugate

To pegylate 5K methoxyPEG-Succinimidyl Butanoate(1) to a lysine residue which is a 29th amino acid of B chain in human insulin (Sigma), the PEG and the human insulin were subjected to a reaction at 25° C. for 1 hours at a molar ratio of 1:2, with a peptide concentration of 2 mg/mL. At this time, 100 mM Na-Borate buffer (pH 9.0) containing 45% isopropanol was used as a reaction medium.

<25-2> Isolation of Positional Isomer

Figure 35:
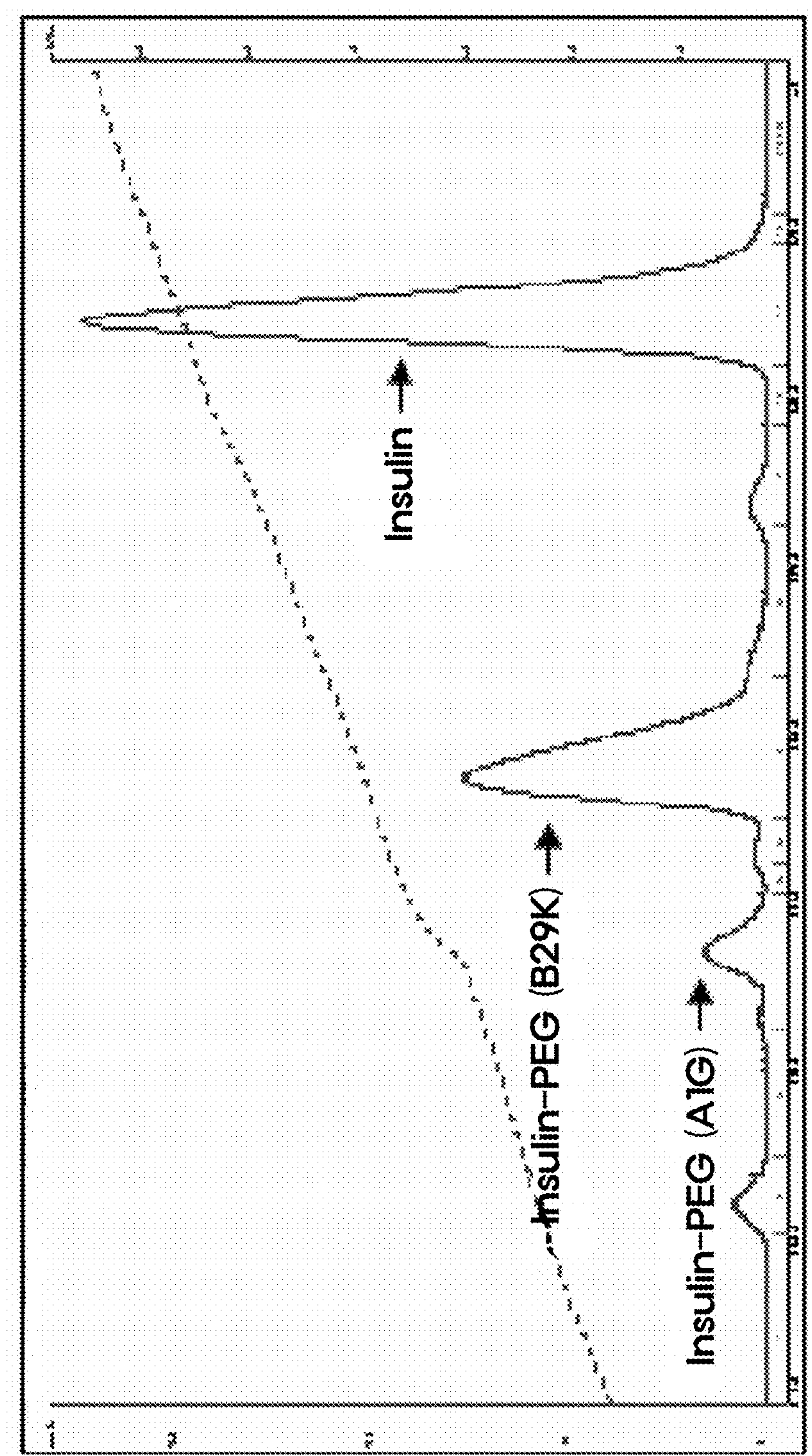
FIG. 35: a purification profile of positional isomers of human insulin-PEG (B29K) using SOURCE S column.

Positional isomers were purified from the reaction mixture by using SOURCE 15S column (XK 16 mL, Amersham Bioscience). The purification procedure was same with that described in Example 23. In this process, ethanol was used in the purification solution to facilitate the isolation of isomers (FIG. 35). The mono-pegylations of eluted peaks were confirmed by SDS-PAGE analysis, and the lysine selectivities were confirmed by peptide mapping method using Glu-C protease (FIG. 36).

As shown in FIG. 36, a #4 part disappeared by PEG-modification at B29K.

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a site-specific physiologically active polypeptide conjugate, comprising the steps of:

i) determining a kind and an amount of a first alcohol and a pH range where a target site conjugate exist more than a non-target site conjugate by identifying a ratio of the target site conjugate and non-target site conjugate , depending on the change of the kind and the amount of the first alcohol and pH in a reaction medium, wherein the target site conjugate is a conjugate of a physiologically active polypeptide and a non-peptidyl polymer, said non-peptidyl polymer binding to a target amino acid residue of the physiologically active polypeptide, and wherein the non-target site conjugate is a conjugate of a physiologically active polypeptide and a non-peptidyl polymer, said non-peptidyl polymer binding to an amino acid residue other than the target amino acid residue of the physiologically active polypeptide;

ii) reacting the physiologically active polypeptide with the non-peptidyl polymer in a reaction medium having the kind and the amount of the first alcohol and the pH range determined in step i); and iii) isolating and purifying the physiologically active polypeptide conjugate from the reaction mixture of step ii) by ion exchange chromatography using a second alcohol, wherein the non-peptidyl polymer is selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, poly (lactic acid), polylactic-glycolic acid, lipid polymers, chitins, hyaluronic acid, and combinations thereof; and wherein the non-peptidyl polymer has a reactive aldehyde, propionaldehyde or butyraldehyde group at both ends thereof.

2. The method of claim 1, wherein the physiologically active polypeptide is selected from the group consisting of insulinotropic peptide, blood factor, digestive hormone, adrenocorticotropic hormone, thyroid hormone, intestinal hormone, cytokine, enzyme, growth factor, neuropeptide, hypophyseotropic hormone, hypophysiotropic hormone, anti-obesity peptide, and anti-viral peptide.

3. The method of claim 1, wherein the physiologically active polypeptide is selected from the group consisting of erythropoietin, granulocyte macrophage-colony stimulating factor, amylin, glucagon, insulin, somatostatin, peptide YY, neuropeptide Y, glucagon-like peptide 1, glucagon-like peptide 2, exendin-4, oxyntomodulin, ghrelin, angiotensin, bradykinin, calcitonin, corticotropin, eledoisin, gastrin, leptin, oxytocin, vasopressin, luteinizing hormone, prolactin, follicle stimulating hormone, parathyroid hormone, secretin, sermorelin, human growth hormone, growth hormone-releasing peptide, granulocyte colony stimulating factor, interferons, interleukins, prolactin-releasing peptide, orexin, thyroid-releasing peptide, cholecystokinin, gastrin-inhibiting peptide, calmodulin, gastrin-releasing peptide, motilin, vasoactive intestinal peptide, atrial natriuretic peptide, brain natriuretic peptide, C-type natriuretic peptide, neurokinin A, neuromedin, renin, endothelin, sarafotoxin peptide, carsomorphin peptide, dermorphin, dynorphin, endorphin, enkepalin, T cell factor, tumor necrosis factor, tumor necrosis factor receptor, urokinase receptor, tumor inhibitory factor, collagenase inhibitor, thymopoietin, thymulin, thymopentin, tymosin, thymic humoral factor, adrenomodullin, allatostatin, amyloid beta-protein fragment, antimicrobial peptide, antioxidant peptide, bombesin, osteocalcin, CART peptide, E-selectin, intercellular adhesion molecule 1, vascular cell adhesion molecule 1, leucokine, kringle-5, laminin, inhibin, galanin, fibronectin, pancreastatin, and fuzeon.

4. The method of claim 1, wherein the physiologically active polypeptide is an exendin, insulin, glucagon-like peptide 1, glucagon-like peptide 2, oxyntomodulin, ghrelin, or calcitonin.

5. The method of claim 4, wherein the physiologically active polypeptide is an exendin, oxyntomodulin, glucagon-like peptide 1, or glucagon-like peptide 2, each having any structure selected from Formulas (I) to (IV):

Formula I

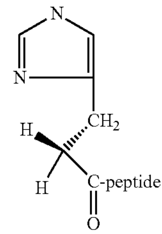

Formula II

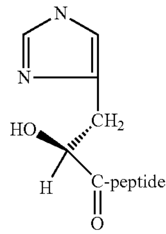

Formula III

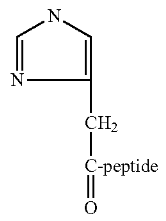

Formula IV

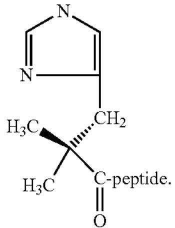

wherein the peptide is exendin, oxyntomodulin, glucagon-like peptide 1, or glucagon-like peptide 2.

6. The method of claim 1, wherein the alcohol used in steps (i) and (ii) is primary, secondary, or tertiary alcohol having a carbon number of one to ten.

7. The method of claim 6, wherein the alcohol is ethanol or isopropanol.

8. The method of claim 1, wherein the alcohol is present in the reaction medium, in an amount of 35% to 60% by volume, based on the total amount of the reaction medium.

9. The method of claim 1, wherein the pH employed in step (i) is 7.0 to 10.0, when the physiologically active polypeptide is an exendin or a derivative thereof.

10. The method of claim 1, wherein the pH employed in step (i) is 7.0 to 10.0, when the physiologically active polypeptide is oxyntomodulin or a derivative thereof.

11. The method of claim 1, wherein the pH employed in step (i) is 4.0 to 10.0, when the physiologically active polypeptide is human insulin or a derivative thereof.

12. The method of claim 1, wherein the pH employed in step (i) is 7.0 to 10.0, when the physiologically active polypeptide is glucagon-like peptide 1 or a derivative thereof.

13. The method of claim 1, wherein the pH employed in step (i) is 7.0 to 10.0, when the physiologically active polypeptide is a glucagon-like peptide 2 or a derivative thereof.

14. The method of claim 1, wherein the site-specific physiologically active polypeptide conjugate is an exendin-4 conjugate in which PEG is linked to Lys27 of SEQ ID NO: 1, a calcitonin conjugate in which PEG is linked to the N-terminal, an oxyntomodulin conjugate in which PEG is linked to Lys27 or Lys30 of SEQ ID NO: 2, human insulin conjugate in which PEG is linked to the N-terminal of Glyl in insulin A chain of SEQ ID NO: 3, or is linked to Lys29 in insulin B-chain of SEQ ID NO: 4, a glucagon-like peptide 1 conjugate in which PEG is linked to Lys34 of SEQ ID NO: 5, or a glucagon-like peptide 2 conjugate in which PEG is linked to Lys30 of SEQ ID NO: 6.

15. The method of claim 1, wherein the non-peptidyl polymer is polyethtylene glycol.

* * * * *

SEQUENCE LISTING

```
<160> NUMBER OF SEQ ID NOS: 6

<210> SEQ ID NO 1
<211> LENGTH: 39
<212> TYPE: PRT
<213> ORGANISM: Heloderma suspectum
<220> FEATURE:
<221> NAME/KEY: CDS
<222> LOCATION: 1..39
<223> OTHER INFORMATION: exendin-4

<400> SEQUENCE: 1

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35


<210> SEQ ID NO 2
<211> LENGTH: 37
<212> TYPE: PRT
<213> ORGANISM: Homo sapiens
<220> FEATURE:
<221> NAME/KEY: CDS
<222> LOCATION: 1..37
<223> OTHER INFORMATION: oxyntomodulin

<400> SEQUENCE: 2
```

```
His Ser Gln Gly Thr Phe Thr Ser Asp Tyr Ser Lys Tyr Leu Asp Ser
  1               5                  10                  15

Arg Arg Ala Gln Asp Phe Val Gln Trp Leu Met Asn Thr Lys Arg Asn
             20                  25                  30

Arg Asn Asn Ile Ala
         35


<210> SEQ ID NO 3
<211> LENGTH: 21
<212> TYPE: PRT
<213> ORGANISM: Homo sapiens
<220> FEATURE:
<221> NAME/KEY: CDS
<222> LOCATION: 1..21
<223> OTHER INFORMATION: Insulin A chain

<400> SEQUENCE: 3

Gly Ile Val Glu Gln Cys Cys Thr Ser Ile Cys Ser Leu Tyr Gln Leu
  1               5                  10                  15

Glu Asn Tyr Cys Asn
             20


<210> SEQ ID NO 4
<211> LENGTH: 30
<212> TYPE: PRT
<213> ORGANISM: Homo sapiens
<220> FEATURE:
<221> NAME/KEY: CDS
<222> LOCATION: 1..30
<223> OTHER INFORMATION: Insulin B chain

<400> SEQUENCE: 4

Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Lys Thr
             20                  25                  30


<210> SEQ ID NO 5
<211> LENGTH: 37
<212> TYPE: PRT
<213> ORGANISM: Homo sapiens
<220> FEATURE:
<221> NAME/KEY: CDS
<222> LOCATION: 1..37
<223> OTHER INFORMATION: Glucagon-like peptide 1

<400> SEQUENCE: 5

His Asp Glu Phe Glu Arg His Ala Glu Gly Thr Phe Thr Ser Asp Val
  1               5                  10                  15

Ser Ser Tyr Leu Glu Gly Gln Ala Ala Lys Glu Phe Ile Ala Trp Leu
             20                  25                  30

Val Lys Gly Arg Gly
         35


<210> SEQ ID NO 6
<211> LENGTH: 33
<212> TYPE: PRT
<213> ORGANISM: Homo sapiens
<220> FEATURE:
<221> NAME/KEY: CDS
<222> LOCATION: 1..33
<223> OTHER INFORMATION: Glucagon-like peptide 2

<400> SEQUENCE: 6
```

-continued

```
His Ala Asp Gly Ser Phe Ser Asp Glu Met Asn Thr Ile Leu Asp Asn
  1               5                  10                  15

Leu Ala Ala Arg Asp Phe Ile Asn Trp Leu Ile Gln Thr Lys Ile Thr
             20                  25                  30

Asp
```